(12) United States Patent
Clements et al.

(10) Patent No.: US 8,198,079 B2
(45) Date of Patent: Jun. 12, 2012

(54) SYNTHETIC EXPRESSION VECTORS FOR INSECT CELLS

(75) Inventors: David Edward Clements, Honolulu, HI (US); Gordon V. L. Wang, Pearl City, HI (US); Carolyn Weeks-Levy, Honolulu, HI (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 280 days.

(21) Appl. No.: 12/451,145

(22) PCT Filed: Apr. 28, 2008

(86) PCT No.: PCT/US2008/005514
§ 371 (c)(1),
(2), (4) Date: Oct. 26, 2009

(87) PCT Pub. No.: WO2008/134068
PCT Pub. Date: Nov. 6, 2008

(65) Prior Publication Data
US 2010/0167389 A1    Jul. 1, 2010

Related U.S. Application Data

(60) Provisional application No. 60/926,621, filed on Apr. 26, 2007.

(51) Int. Cl.
*C12N 15/63* (2006.01)
(52) U.S. Cl. .................................................. 435/320.1
(58) Field of Classification Search .................. None
See application file for complete search history.

(56) References Cited

U.S. PATENT DOCUMENTS
5,244,805 A * 9/1993 Miller ........................ 435/320.1
2006/0228400 A1 10/2006 Lanahan et al.

FOREIGN PATENT DOCUMENTS
WO    2006/127980 A2    11/2006
WO    2007/022425 A2    2/2007

OTHER PUBLICATIONS

Bernard AR, Kost TA, Overton L, Cavegn C, Young J, Bertrand M, Yahia-cherif Z, Chabert C and Mills A. Recombinant protein expression in *Drosophila* cell line: comparison with the baculovirus system. Cytotechnology. 1994; 15:139-144.
Culp JS, Johansen H, Hellmig B. Regulated expression allows high level production and secretion of HIV gp120 envelope glycoprotein in *Drosophila* Schneider cells. Biotechnology. 1991; 9:173-177.
Deo YK, Park EY. Multiple co-transfection and co-expression of human α-1,3-N-acetylglucosaminyltransferase with human calreticulin chaperone cDNA in a single step in insect cells. Biotechnol. Appl. Biochem. 2006; 43: 129-135.
Edelman GM, Meech R, Owens GC, and Jones FS. Synthetic promoter elements obtained by nucleotide sequence variation and selection for activity. Proc Natl Acad Sci. 2000; 97: 3038-3043.
Farrell PJ, Lu M, Prevost J, Brown C, Behie L, Iatrou K. High-level expression of secreted glycoproteins in transformed lepidopteran insect cells using a novel expression vector. Biotechnology and Bioengineering. 1998; 60 (6): 656-663.
FitzGerald PC, Sturgill D, Shyakhtenko A, Oliver B, Vinson C. Comparative genomics of *Drosophila* and human core promoters. Genome Biology. 2006; 7:R53.
Gardsvoll H, Werner F, Sondergaard L, Dano K, Ploug M. Characterization of low-glycosylated forms of soluble human urokinase receptor expressin in *Drosophila* Schneider 2 cells after deletion of glycosylation-sites. Protein Expression and Purification. 2004; 34:284-295.
Ikonomou L, Schneider Y-J, Agathos SN. Insect cell culture for industrial production of recombinant proteins. Appl. Microbiol. Biotechnol. 2003; 62:1-20.
Incardona, J.P. and T.L. Rosenberry. Construction and characterization of secreted and chimeric transmembrane forms of *Drosophila* acetylcholinesterase: a large truncation of the C-terminal signal peptide does not eliminate glycoinositol phospholipid anchoring. Mol. Biol. of the Cell 1996; 7:595-611.
Ivey-Hoyle, M. Recombinant gene expression in cultured *Drosophila melanogaster* cells. Curr. Opin. Biotechnol. 1991; 2:704-707.
Johansen HA, van der Straten R, Sweet R, Otto E, Maroni G, Rosenberg M. Regulated expression at high copy number allows production of a growth-inhibitory oncogene product in *Drosophila* Schneider cells. Genes and Development. 1989; 3:882-889.
Juven-Gershon T, Hsu JY, Kadonaga JT. Perspectives on the RNA polymerase II core promoter. Biochem Soc. Trans. 2006; 34:1047-1050.
Kralova, Jarmila, et al., Complex regulatory element within the γE- and γF-crystallin enhancers mediates Pax6 regulation and is required for induction by retinoic acid, Gene, 2002, vol. 286, pp. 271-282.
Li, Bin, et al., Expression of human dopamine α-hydroxylase in *Drosophila* Schneider 2 cells, Biochem. J., 1996, vol. 313, pp. 57-64.

(Continued)

*Primary Examiner* — Scott Long
(74) *Attorney, Agent, or Firm* — Alysia A. Finnegan; Sheldon O. Heber

(57) ABSTRACT

The present invention is directed at optimized expression vectors for the expression of native-like heterologous proteins in insect cells. Compositions of the invention are nucleotide sequences representing elements of an expression vector that when combined results in enhanced expression and secretion of heterologous proteins. The elements include sequences that define transcriptional activators, core promoters, secretion signals, and 3' untranslated regions that are functional in insect cells. The elements contained in the optimized vectors are all synthetically derived or are modified variants of naturally occurring insect sequences. The expression vectors are useful for the expression of native-like proteins when protein encoding nucleotide sequences are operatively linked to the vectors. These vectors can be used to transform insect cells, which can then be cultured to produce the desired protein product. The expressed native-like proteins can be used in diagnostic, vaccine or other applications requiring large amounts of high quality proteins.

10 Claims, 4 Drawing Sheets

OTHER PUBLICATIONS

Lim CY, Santoso B, Boulay T, Dong E, Ohler U, Kadonaga JT. The MTE, a new core promoter element for transcription by RNA polymerase II. Genes and Dev. 2004; 18: 1606-1617.

Matsumoto, K., et al., Necdin acts as a transcriptional repressor that interacts with multiple guanosine clusters, Gene, 2001, vol. 272, pp. 173-179.

Modis Y, Ogata S, Clements D, Harrison SC. A ligand-binding pocket in the dengue virus envelope glycoprotein. Proc. Natl. Acad. Sci. USA. 2003; 100:6986-6991.

Modis Y, Ogata S, Clements D, Harrison SC. Structure of the dengue virus envelope protein after membrane fusion. Nature. 2004; 427(6972): 313-319.

Ohler U, Liao G, Niemann H, Rubin GM. Computational analysis of core promoters in the Drosophila genome. Genome Biol. 2002; 3(12): research0087.1-0087.12.

Schmetzer O, Moldenhauer G, Riesenberg R, Pires JR, Schlag P, Pezzutto A. 2005. Quality of recombinant protein determines the amount of autoreactivity against the tumor-associated epithelial cell adhesion molecule antigen: low frequency of antibodies against the natural protein. The Journal of Immunology. 2005; 174: 942-952.

Schmidt FR. Recombinant expression systems in the pharmaceutical industry. Appl Microbiol Biotechnol. 2004; 65:363-372.

Schneider IJ. Cell lines derived from late embryonic stages of Drosophila melanogaster. J. Embryol. Exp. Morph. 1972; 27:353-365.

Smale ST, Kadonaga JT. The RNA polymerase II core promoter. Annu. Rev. Biochem. 2003; 72: 449-479.

Teunissen, Birgit E.J., et al., Analysis of the rat connexin 43 proximal promoter in neonatal cardiomyocytes, Gene, 2003, vol. 322, pp. 123-136.

Tornoe J, Kusk P, Johansen TE, Jensen PR. Generation of a synthetic mammalian promoter library by modification of sequences spacing transcription factor binding sites. Gene. 2002; 297: 21-32.

Werner, T., Models for prediction and recognition of eukaryotic promoters, Institute of Mammalian Genome, 1999, vol. 10. pp. 168-175.

Xu T, Logsdon NJ, Water MR. Structure of insect-cell-derived IL-22. Acta Crystallogr D Biol Crystallogr. 2005; 61(pt 7): 942-50.

Gershon, et al., Rational design of a super core promoter that enhances gene expression, Nature Methods, 2006, vol. 3, No. 11, pp. 917-922.

* cited by examiner

FIGURE 1. 3XR MRE-3XR MRE-SCP1-TolloMTEΔ111 Synthetic Promoter

```
1                                                                 65
|                                                                  |
GCCGGCGTGTGCAAAAGAGCCGGCGTGTGCAAAAGAGCCGGCGTGTGCAAAAGAATCAAACTAGA
<----Rev MRE------<----Rev MRE------<----Rev MRE------11nt spacer 66                                                                130
|                                                                  |
GCCGGCGTGTGCAAAAGAGCCGGCGTGTGCAAAAGAGCCGGCGTGTGCAAAAGAATCAAACTAGA
<----Rev MRE------<----Rev MRE------<----Rev MRE------11nt spacer 131                                                               2(
|                                   +1                             |
GGGCGCCTATAAAAACAGCGGCGCTCCAGGTGCAGGCATCAGTCGTTAGCCAGTCGCCGAGCCGAGCGGTTCG
 BRE    TATA                           Inr                MTE       DPE 204                  236
|                     |
AAGTGATTTTGCAAACCGAAGCTTAACAACATG
                            Kozak Met
```

FIGURE 2. 3XR MRE-3XR MRE -SCP7 Synthetic Promoter

```
1                                                                 65
|                                                                  |
GCCGGCGTGTGCAAAAGAGCCGGCGTGTGCAAAAGAGCCGGCGTGTGCAAAAGAATCAAACTAGA
<----Rev MRE------<----Rev MRE------<----Rev MRE------11nt spacer 66                                                                130
|                                                                  |
GCCGGCGTGTGCAAAAGAGCCGGCGTGTGCAAAAGAGCCGGCGTGTGCAAAAGAATCAAACTAGA
<----Rev MRE------<----Rev MRE------<----Rev MRE------11nt spacer 131                                                               2(
|                                   +1                             |
CAAAATGTATAAAAACAGCGGCGCTCCAGGTGCAGGCAGCATCAGTTAGCCAGTCGCCGAGCCGAGCTGAATA
       TATA                            Inr                MTE 204                  236
|                     |
AAGTGATTTTGCAAACCGAAGCTTAACAACATG
                            Kozak Met
```

FIGURE 3. Comparison of pMTtPA, pHBI-10, and pHBI-11 Expression Vectors

| ELEMENT | pMTtPA | pHBI-10 | pHBI-11 |
| --- | --- | --- | --- |
| Proximal Promoter | *Drosophila* MtnA | Synthetic MRE repeats | Synthetic MRE repeats |
| Core Promoter | *Drosophila* MtnA | Synthetic SCP1-TolloMTEΔ111 | Synthetic SCP7 |
| 5'UTR | *Drosophila* MtnA | Δ111 | Δ111-7 |
| Secretion Signal | Human tPA | Synthetic 1R5L(H) | Synthetic 1R5L(H) |
| 3'UTR | SV-40 Early | Optimized CLP | Optimized CLP |

FIGURE 4. pHBI-10 Plasmid Map
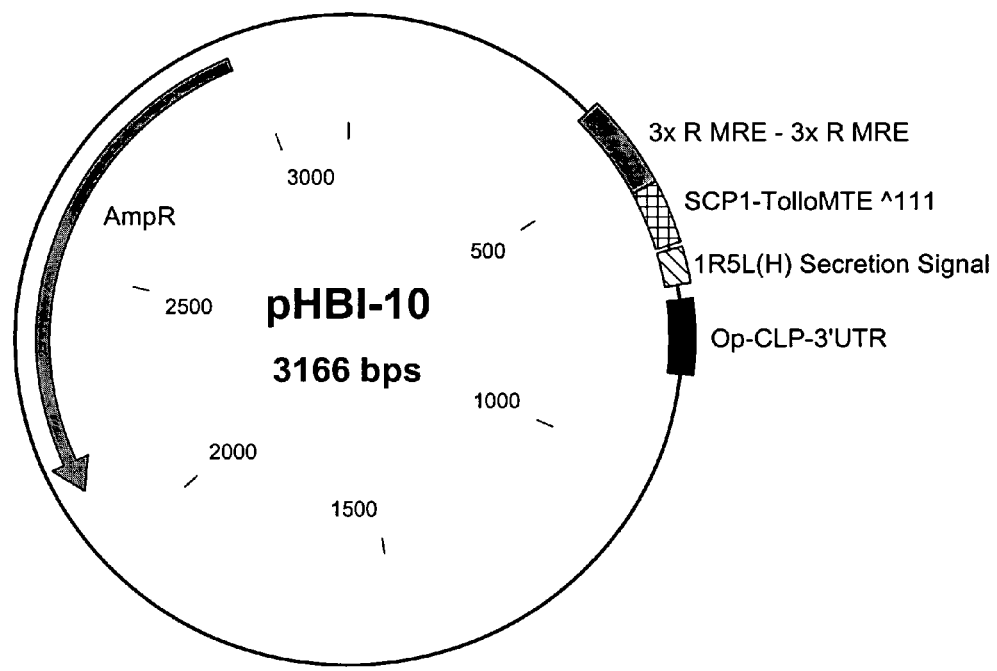

FIGURE 5. pHBI-11 Plasmid Map
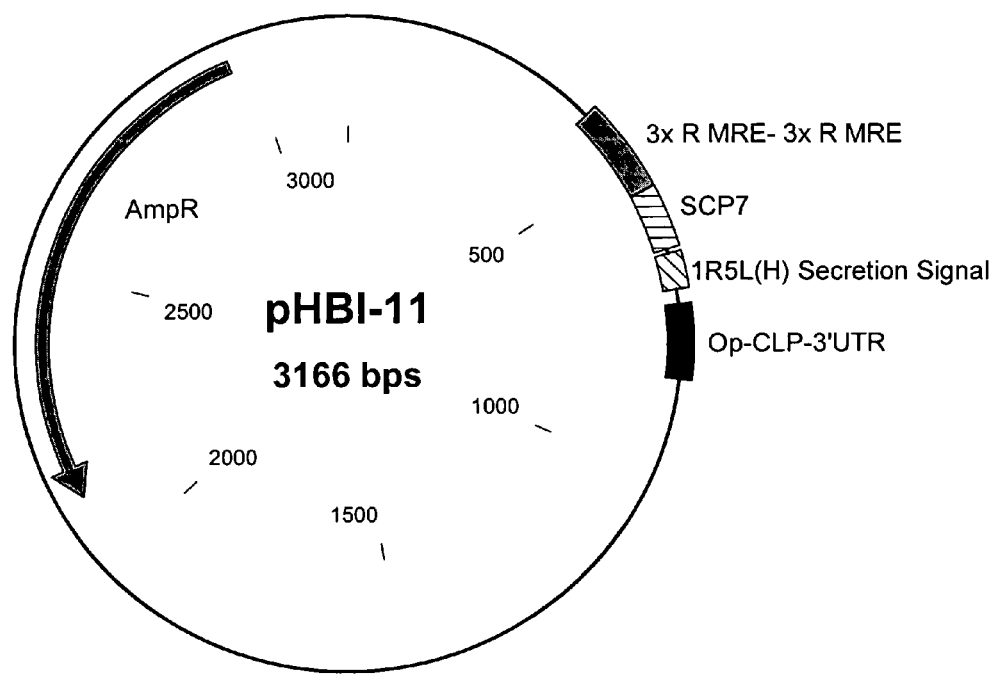

SEQUENCE LISTING

```
<160> NUMBER OF SEQ ID NOS: 22

<210> SEQ ID NO 1
<211> LENGTH: 230
<212> TYPE: DNA
<213> ORGANISM: Artificial Sequence
<220> FEATURE:
<223> OTHER INFORMATION: Synthetic core promoter

<400> SEQUENCE: 1
gggcgcctat aaaaacagcg gcgctccagg tgcaggcatc agtcgttagc cagtcgccga      60
acggaacggt tcgaagtgat tttgcaaacc gtgtgattag tttgaagcaa gcgttgtcac     120
gagcaacggg tgaaagtgta ccacgactac tacgtgccca aggtctttag tgtcctcttt     180
tttcctgtac gctgcgaagc accgatagaa aactgcacaa gcttaacaac                230

<210> SEQ ID NO 2
<211> LENGTH: 103
<212> TYPE: DNA
<213> ORGANISM: Artificial Sequence
<220> FEATURE:
<223> OTHER INFORMATION: Synthetic core promoter

<400> SEQUENCE: 2
gggcgcctat aaaaacagcg gcgctccagg tgcaggcatc agtcgttagc cagtcgccga      60
gccgagcggt tcgaagtgat tttgcaaacc gaagcttaac aac                       103

<210> SEQ ID NO 3
<211> LENGTH: 103
<212> TYPE: DNA
<213> ORGANISM: Artificial Sequence
<220> FEATURE:
<223> OTHER INFORMATION: Synthetic core promoter

<400> SEQUENCE: 3
caaaatgtat aaaaacagcg gcgctccagg tgcaggcagc atcagttagc cagtcgccga      60
```

```
gccgagcgtg aataagtgat tttgcaaacc gaagcttaac aac                      103
```

<210> SEQ ID NO 4
<211> LENGTH: 63
<212> TYPE: DNA
<213> ORGANISM: Artificial Sequence
<220> FEATURE:
<223> OTHER INFORMATION: Synthetic 5 'UTR sequence

<400> SEQUENCE: 4

```
agtcgttagc cagtcgccga gccgagcggt tcgaagtgat tttgcaaacc gaagcttaac    60
aac                                                                  63
```

<210> SEQ ID NO 5
<211> LENGTH: 63
<212> TYPE: DNA
<213> ORGANISM: Artificial Sequence
<220> FEATURE:
<223> OTHER INFORMATION: Synthetic 5 'UTR sequence

<400> SEQUENCE: 5

```
atcagttagc cagtcgccga gccgagcgtg aataagtgat tttgcaaacc gaagcttaac    60
aac                                                                  63
```

<210> SEQ ID NO 6
<211> LENGTH: 119
<212> TYPE: DNA
<213> ORGANISM: Artificial Sequence
<220> FEATURE:
<223> OTHER INFORMATION: Synthetic proximal promoter

<400> SEQUENCE: 6

```
gccggcgtgt gcaaaagagc cggcgtgtgc aaaagagccg gcgtgtgcaa aagaatcaaa    60
ctagagccgg cgtgtgcaaa agagccggcg tgtgcaaaag agccggcgtg tgcaaaaga   119
```

<210> SEQ ID NO 7
<211> LENGTH: 54
<212> TYPE: DNA
<213> ORGANISM: Artificial Sequence
<220> FEATURE:
<223> OTHER INFORMATION: Synthetic secretion signal nucleotide sequence

<400> SEQUENCE: 7

```
atgcgcacca tcatcgccct gctgctcctg ctcaccgtgt ccggcgctca cgga          54
```

<210> SEQ ID NO 8
<211> LENGTH: 18
<212> TYPE: PRT
<213> ORGANISM: Artificial Sequence
<220> FEATURE:
<223> OTHER INFORMATION: Synthetic secretion signal peptide sequence

<400> SEQUENCE: 8

Met Arg Thr Ile Ile Ala Leu Leu Leu Leu Leu Thr Val Ser Gly Ala
 1               5                  10                  15

His Gly

<210> SEQ ID NO 9
<211> LENGTH: 117
<212> TYPE: DNA
<213> ORGANISM: Artificial Sequence
<220> FEATURE:
<223> OTHER INFORMATION: Optimized 3 'UTR sequence

<400> SEQUENCE: 9
agtgggagtc caatttgatt tatgtatagc tgaccatgtg aataaaatgc ttgatcaata    60
aatatatttg tcccatttat atttgtaatg tcataaagtg cctcagaaca cataatg      117

<210> SEQ ID NO 10
<211> LENGTH: 429
<212> TYPE: DNA
<213> ORGANISM: Artificial Sequence
<220> FEATURE:
<223> OTHER INFORMATION: Optimized expression cassette for Drosophila

<400> SEQUENCE: 10
gccggcgtgt gcaaaagagc cggcgtgtgc aaaagagccg gcgtgtgcaa aagaatcaaa    60
ctagagccgg cgtgtgcaaa agagccggcg tgtgcaaaag agccggcgtg tgcaaaagaa   120
tcaaactaga gggcgcctat aaaaacagcg gcgctccagg tgcaggcatc agtcgttagc   180
cagtcgccga gccgagcggt tcgaagtgat tttgcaaacc gaagcttaac aacatgcgca   240
ccatcatcgc cctgctgctc ctgctcaccg tgtccggcgc tcacggatcc ggcggcggta   300
ccatcactcg agagtgggag tccaatttga tttatgtata gctgaccatg tgaataaaat   360
gcttgatcaa taaatatatt tgtcccattt atatttgtaa tgtcataaag tgcctcagaa   420
cacataatg                                                           429

<210> SEQ ID NO 11
<211> LENGTH: 429
<212> TYPE: DNA
<213> ORGANISM: Artificial Sequence
<220> FEATURE:
<223> OTHER INFORMATION: Optimized expression cassette for Drosophila

<400> SEQUENCE: 11
gccggcgtgt gcaaaagagc cggcgtgtgc aaaagagccg gcgtgtgcaa aagaatcaaa    60
ctagagccgg cgtgtgcaaa agagccggcg tgtgcaaaag agccggcgtg tgcaaaagaa   120
tcaaactaga caaaatgtat aaaaacagcg gcgctccagg tgcaggcagc atcagttagc   180
cagtcgccga gccgagcgtg aataagtgat tttgcaaacc gaagcttaac aacatgcgca   240
ccatcatcgc cctgctgctc ctgctcaccg tgtccggcgc tcacggatcc ggcggcggta   300
ccatcactcg agagtgggag tccaatttga tttatgtata gctgaccatg tgaataaaat   360
gcttgatcaa taaatatatt tgtcccattt atatttgtaa tgtcataaag tgcctcagaa   420
cacataatg                                                           429

<210> SEQ ID NO 12
<211> LENGTH: 236
<212> TYPE: DNA
<213> ORGANISM: Artificial Sequence
<220> FEATURE:
<223> OTHER INFORMATION: 3XR MRE-3XR MRE-SCP1-TolloMTE delta 111
      Synthetic Promoter

<400> SEQUENCE: 12
gccggcgtgt gcaaaagagc cggcgtgtgc aaaagagccg gcgtgtgcaa aagaatcaaa    60
ctagagccgg cgtgtgcaaa agagccggcg tgtgcaaaag agccggcgtg tgcaaaagaa   120
tcaaactaga gggcgcctat aaaaacagcg gcgctccagg tgcaggcatc agtcgttagc   180
cagtcgccga gccgagcggt tcgaagtgat tttgcaaacc gaagcttaac aacatg       236

<210> SEQ ID NO 13
<211> LENGTH: 236
<212> TYPE: DNA

```
<213> ORGANISM: Artificial Sequence
<220> FEATURE:
<223> OTHER INFORMATION: 3XR MRE-3XR MRE -SCP7 Synthetic Promoter

<400> SEQUENCE: 13
gccggcgtgt gcaaaagagc cggcgtgtgc aaaagagccg gcgtgtgcaa aagaatcaaa      60
ctagagccgg cgtgtgcaaa agagccggcg tgtgcaaaag agccggcgtg tgcaaaagaa     120
tcaaactaga caaaatgtat aaaaacagcg gcgctccagg tgcaggcagc atcagttagc     180
cagtcgccga gccgagctga ataaagtgat tttgcaaacc gaagcttaac aacatg        236

<210> SEQ ID NO 14
<211> LENGTH: 12
<212> TYPE: DNA
<213> ORGANISM: Artificial Sequence
<220> FEATURE:
<223> OTHER INFORMATION: Sequence preceding ATG in pMTtPA

<400> SEQUENCE: 14
tgtgaagcaa tc                                                         12

<210> SEQ ID NO 15
<211> LENGTH: 12
<212> TYPE: DNA
<213> ORGANISM: Artificial Sequence
<220> FEATURE:
<223> OTHER INFORMATION: HindIII site + consensus Kozak sequence

<400> SEQUENCE: 15
aagcttaaca ac                                                         12

<210> SEQ ID NO 16
<211> LENGTH: 24
<212> TYPE: DNA
<213> ORGANISM: Artificial Sequence
<220> FEATURE:
<223> OTHER INFORMATION: synthetic DRE containing proximal promoter

<400> SEQUENCE: 16
ctgcctgcta tcgatagatt cagg                                            24

<210> SEQ ID NO 17
<211> LENGTH: 18
<212> TYPE: DNA
<213> ORGANISM: Artificial Sequence
<220> FEATURE:
<223> OTHER INFORMATION: Portion of MtnA proximal promoter in pMTtPA
      delta Xho

<400> SEQUENCE: 17
tcttttgcac acgccggc                                                   18

<210> SEQ ID NO 18
<211> LENGTH: 18
<212> TYPE: DNA
<213> ORGANISM: Artificial Sequence
<220> FEATURE:
<223> OTHER INFORMATION: Reverse MRE Sequence

<400> SEQUENCE: 18
gccggcgtgt gcaaaaga                                                   18

<210> SEQ ID NO 19
<211> LENGTH: 11
<212> TYPE: DNA
<213> ORGANISM: Artificial Sequence
```

```
<220> FEATURE:
<223> OTHER INFORMATION: Synthetic spacer

<400> SEQUENCE: 19
atcaaactag a                                                                11

<210> SEQ ID NO 20
<211> LENGTH: 17
<212> TYPE: PRT
<213> ORGANISM: Artificial Sequence
<220> FEATURE:
<223> OTHER INFORMATION: 1R4L signal peptide

<400> SEQUENCE: 20

Met Arg Thr Ile Ile Ala Leu Leu Leu Leu Thr Val Ser Gly Ala Gln
1               5                   10                  15

Gly

<210> SEQ ID NO 21
<211> LENGTH: 18
<212> TYPE: PRT
<213> ORGANISM: Artificial Sequence
<220> FEATURE:
<223> OTHER INFORMATION: 1R5L signal peptide

<400> SEQUENCE: 21

Met Arg Thr Ile Ile Ala Leu Leu Leu Leu Leu Thr Val Ser Gly Ala
1               5                   10                  15

Gln Gly

<210> SEQ ID NO 22
<211> LENGTH: 19
<212> TYPE: PRT
<213> ORGANISM: Artificial Sequence
<220> FEATURE:
<223> OTHER INFORMATION: 2R5L signal peptide

<400> SEQUENCE: 22

Met Arg Arg Thr Ile Ile Ala Leu Leu Leu Leu Leu Thr Val Ser Gly
1               5                   10                  15

Ala Gln Gly
```

SYNTHETIC EXPRESSION VECTORS FOR INSECT CELLS

RELATED APPLICATIONS

This application is a §371 National Stage Application of PCT/US2008/05514, filed 4 Apr. 2008, which claims the benefit of U.S. provisional patent application Ser. No. 60/926,621, entitled "Synthetic Expression Vectors for Insect Cells", filed on 26 Apr. 2007, the disclosures and drawings of which prior application are hereby incorporated by referenced in their entirety.

GOVERNMENT RIGHTS

The invention was made under contract number W81XWH-06-2-0035 with USAMRAA, a U.S. Government agency.

FIELD OF THE INVENTION

The invention relates generally to the design of improved expression vectors for production of heterologous proteins in insect cells. The improved expression vectors are composed of a series of regulatory elements that are synthetic in origin or optimized and assembled in a manner that provides for high levels of recombinant protein expression. In addition, this invention relates to the production of recombinant subunit proteins utilizing these improved expression vectors for use in vaccine formulations.

REFERENCE TO SEQUENCE LISTING SUBMITTED ELECTRONICALLY

The sequence listing of the present application is submitted electronically via EFS-Web as an ASCII formatted sequence listing with a file name "MRLIFD00053USPCT_SEQLIST__29FEBRUARY2012.TXT", creation date of Feb. 29, 2012, and a size of 6.91 KB. This sequence listing submitted via EFS-Web is part of the specification and is herein incorporated by reference in its entirety.

BACKGROUND OF THE INVENTION

A number of heterologous cell expression systems have been developed to express and secrete recombinant proteins. In general, systems based on eukaryotic host cells are employed for the expression of eukaryotic proteins that require proper folding and post-translation modifications, thus allowing for production of "native-like" proteins. There are four primary eukaryotic host cell types that are typically utilized; fungal including yeast, insect, plant, and mammalian.

The choice of a recombinant protein expression system to employ is dependent on the desired application. The system of choice must meet key criteria such as proper folding and processing, consistency, and productivity (cost effectiveness) of the desired protein product (Schmidt, *Appl. Microbiol. Biotechnol.* (2004) 65:363-372). Insect cell-based expression systems have the potential to meet capacity requirements based on ease of culture, higher tolerance to osmolality and by-product concentrations during large scale culture, and generally higher expression levels (Ikonomou et al., *Appl. Microbiol Biotechnol.* (2003) 62:1-20). Recently the use of expression systems based on insect cells has become more common. These systems provide most of the characteristics desired of eukaryotic systems, but have added benefits such as lower cost of goods. Insect cell systems are either based on infection of host cells with insect virus vectors (e.g. baculovirus) or on the generation of stable cell lines by integration of expression plasmids into the genome of the host cells.

The baculovirus expression system (BES) has emerged as the primary insect cell culture system utilized for recombinant protein expression. This system is based on the use of vectors derived from the insect viruses known as baculovirus. These vectors are used to generate recombinant viruses that encode the desired protein product. The recombinant viruses are used to infect host insect cells that then express the desired recombinant proteins. While there are advantages to this system in regards to ease of cloning and "time to product", there are also several disadvantages. The primary challenge in the use of BES is that it is based on the viral infection of the host cells. This results in cellular lysis and cell death 72-96 hrs post infection (Farrell et al., *Biotech. Biogen.* (1998) 60:656-663; Deo and Park, *Biotechnol. Appl. Biochem.* (2006) 43:129-135). As a result, during the late stages of infection the processing machinery of the insect cells is compromised to the extent that the processing of the desired product is also compromised. This limits the time that the cells can produce product and possibly more importantly leads to altered forms of the product being produced. Furthermore, the lysis of cells releases cellular enzymes that can also affect the quality of the desired product.

The use of stably transformed insect cells for the expression of recombinant proteins is an alternative to the use of BES. Expression systems based on stably transformed insect cell lines are non-lytic and provides for steady long term production of secreted products that require proper folding and post translational modifications. The secretion of the product into the culture medium provides a cleaner starting material for the purification process and allows for the final protein product to be purified with basic methods. This leads to products that are of higher quality (Kirkpatrick and Shatzman in *Gene Expression Systems: Using Nature for the Art of Expression* (1999) pp 289-330).

The *Drosophila melanogaster* cell expression system ("*Drosophila* expression system") is an established heterologous protein expression system based on the use of expression vectors containing *Drosophila* promoters and *Drosophila* S2 cells ("S2 cells") (Schneider, *Embryol. Exp. Morph.* (1972) 27:353-365). S2 cells are transformed with these vectors in order to establish stable cell lines expressing proteins corresponding to the heterologous sequences introduced into the vector (Johansen, H. et al., *Genes Dev.* (1989) 3:882-889; Ivey-Hoyle, M., *Curr. Opin. Biotechnol.* (1991) 2:704-707; Culp, J. S., et al., *Biotechnology (NY)* (1991) 9:173-177; U.S. Pat. Nos. 5,550,043; 5,681,713; 5,705,359; 6,046,025). This insect cell expression system has been shown to successfully produce a number of proteins from different sources. Examples of proteins that have been successfully expressed in the *Drosophila* S2 cell system include HIV gp120 (Culp, J. S., et al., *Biotechnology (NY)* (1991) 9:173-177; Ivey-Hoyle, M., *Curr. Opin. Biotechnol.* (1991) 2:704-707), human dopamine β-hydrolase (Bin et al., *Biochem. J.* (1996) 313:57-64), human vascular cell adhesion protein (Bernard et al., *Cytotechnol.* (1994) 15:139-144). In each of these examples, expression levels were greater than other expression systems that had been previously utilized.

In addition to high levels of expression, the *Drosophila* expression system has been shown to be able to express heterologous proteins that maintain native-like biological function (Bin et al., *Biochem. J.* (1996) 313:57-64), (Incardona and Rosenberry, *Mol. Biol. Cell.* (1996) 7:595-611). More recent examples have shown by means of X-ray crystallography studies that this expression system is capable of producing molecules with native-like structure (Modis et al., *Proc. Natl. Acad. Sci. USA* (2003) 100:6986-6991), (Modis et al., *Nature* (2004) 427:313-319), (Xu et al., *Acta. Crystallogr. D Biol. Crystallogr* (2005) 61:942-950). Two other recent publications have also demonstrated the ability of the *Drosophila* expression system to produce high quality products. In the first report, Schmetzer et al. (*J. Immun.* (2005) 174: 942-952) compares baculovirus-expressed EpCAM protein to *Drosophila*-expressed EpCAM protein for protein folding and native conformation. Specifically, BES-expressed EpCAM and *Drosophila*-expressed EpCAM were compared to denatured *Drosophila*-expressed EpCAM. It was determined that the BES-expressed EpCAM was in a partial folded state relative to the non-denatured and denatured *Drosophila*-expressed EpCAM protein. This indicates that the BES-expressed protein is in an incompletely folded state. The *Drosophila*-expressed EpCAM protein on the other hand adopted a more completely folded state. The authors of this paper considered the *Drosophila*-expressed protein to be in the "natural" state while the baculovirus-expressed protein was not. In the second report, Gardsvoll et al. (*Prot. Exp. Purif.* (2004) 34:284-295) demonstrate that the expression of the urokinase-type plasminogen activator receptor (uPAR) in S2 cells results in a more homogeneous product in regards to glycosylation (5 N-linked sites) than uPAR expressed in CHO cells.

Based on the body of work utilizing *Drosophila* S2 cells as host cells for the expression of heterologous proteins, it is clear that these cells have many characteristics that are desirable in an expression system. In surveying the published reports utilizing these cells to produce recombinant proteins, the expression level of the protein products is typically in the range of 5 to 50 µg/ml. To have a protein production system that can meet the demanding needs of biotech manufacturing, higher levels of expression are desirable. To achieve consistently higher expression levels would require the optimization of any or all of the following, host cells line, growth medium, or expression vectors.

The development of any heterologous protein expression system requires the assembly of various regulatory control elements (hereafter, alternatively called "regulatory elements" or "control elements", or simply "elements", including the singular form of each) into expression vectors that drive the expression of the desired recombinant protein product. These regulatory control elements include transcriptional activators and enhancers, transcriptional initiator and termination elements, translational start and stop elements, and secretion signal leader sequences. The five main regulatory control elements of an expression vector for the secretion of recombinant protein products are 1) proximal promoter, 2) core promoter 3) 5' untranslated region 4) secretion signal peptide and 5) 3' untranslated region. For each one of these elements any optimization must first be done independently. Once individual elements are optimized, they must be assembled and tested to ensure that the assembly of given elements is compatible and capable of directing efficient expression of the desired recombinant protein products. In the assembly of the various combinations of elements it is also important that the elements are "operably linked". "Operably linked" refers to functional linkage between the various elements in a manner that retains the function of each individual elements as well as the function of the combined elements as many transcriptional and translational functions are the result of the processing from one element to the next. Therefore, "operably linked" means that the nucleic acid sequences of the various elements are linked and contiguous and, where necessary, are linked contiguously to maintain an appropriate protein encoding reading frame.

While many successful expression vectors have been developed, fully optimized systems are less common. Furthermore, most developed systems are based on the use of naturally occurring sequences, i.e. the various regulatory elements are taken from existing (naturally occurring) gene sequences. Over the past several years the use of synthetic sequences has been employed as a means to develop optimized expression vectors.

A "promoter" is composed of two basic parts, the core promoter and the proximal promoter. The promoter is located upstream of the coding sequence of a given gene. The core promoter is defined as the minimal nucleotide sequence that is capable of directing accurate transcriptional initiation of a given gene. The core promoter in eukaryotes is responsible for directing initiation by the RNA polymerase II complex. The core promoter is generally delineated as the sequence spanning the transcription initiation site (INR), more specifically the sequence 35 to 45 nucleotides upstream and downstream of the INR (total length of 70 to 90 nucleotides). The region bounded by the core promoter may contain one or more of the following conserved regulatory motifs, TFIIB recognition element (BRE), TATA box, initiator (INR), motif ten element (MTE), downstream promoter element (DPE), and downstream core element (DCE). Although certain nucleotide sequences within a regulatory control element have art-recognized names that include the word "element", such sequences are herein called, in general terms, "motifs"; specific art-recognized names (e.g., BRE, MTE, DPE, and DCE) have the same meaning herein as in the cited references, even though they are called "motifs" herein, e.g., "MTE motif". The role and composition of core promoters and their constituent individual motifs have been reviewed by Ohler et al. (*Genome Biol.*, (2002) 3:1-12), Smale and Kadonaga (*Ann. Rev. Biochem.* (2003) 72:449-479), FitzGerald et al. (*Genome Biol.* (2006) 7:R53), Gershenzon et al. (*BMC Genomics* (2006) 7:161) and Juven-Gershon et al. (*Biochem. Soc. Trans.* (2006) 34:1047-1050). Studies defining the DPE motif (Kutach and Kadonaga, *Mol. Cell. Biol.* (2000) 20:4754-4764) and the MTE motif (Lim et al., *Genes Dev.* (2004) 18:1606-1617) have also been reported. While the core promoters of most genes contain one or more of these motifs in various combinations, there are a small percentage of genes that do not contain any of these motifs. In surveys of core promoters from several organisms it is clear that no universal core promoter, or universal subset of motifs comprising a core promoter, exists; however, the INR motif is the most common (FitzGerald et al., *Genome Biol.* (2006) 7:R53) motif found in core promoters.

The proximal promoter in eukaryotes is generally defined as the sequence that is immediately upstream of the core promoter. The length of the proximal promoter is highly variable. The proximal promoter is composed of transcriptional activator motifs that recruit transcription factors which in turn activate the polymerase initiation complex which is bound to the core promoter region. The nature and number of the transcriptional activator motifs is highly varied for a given promoter.

The optimization of promoters can be accomplished by systematic substitution and testing of various elements or motifs, the use of synthetic promoter libraries, or random substitution of individual regulatory elements or motifs. Examples of these different approaches for the development of optimized or synthetic promoter have been reported. In the work of Li et al. (*Nature Biotechnol.* (1999) 17:241-245) an approach of evaluating randomly assembled transcription factor binding sites to drive transcription of muscle specific promoters was reported. Edelman et al. (*Proc. Natl. Acad. Sci.* (2000) 97:3038-3043) describe a high-throughput selection procedure to select synthetic proximal promoters that enhance the transcriptional activity of a core promoter. Tornoe et al. (*Gene* (2002) 297:21-32) built a set of synthetic promoters for use in mammalian cells that combined viral and human promoter elements. The synthetic mammalian promoters were further optimized by substituting consensus sequences and randomizing other non-consensus sequences to obtain promoters with variable activity. In the development of synthetic promoters for gene expression in *Lactobacillus*, Rud et al. (*Microb.* (2006) 152:1011-1019) utilized consensus sequences for regulatory elements along with randomization of the spacer sequences between the regulatory elements to improve the performance of the promoter. In this manner they were able to identify synthetic promoters that had increased activity. In work by Juven-Gershon et al. (*Nature Methods* (2006) 3:917-922) the development of an optimized core promoter is achieved by combining core promoter motifs from different *Drosophila* and viral genes. This work centered on the use of the MTE motif (Lim et al., *Genes Dev.* (2004) 18:1606-1617) of the core promoter. This strategy resulted in core promoters with increased transcriptional activity. Based on these reports, it is clear that there is a need to experimentally determine what regulatory elements, and constituent motifs, constitute a functional promoter. This includes which combinations of motifs are used, in which order the motifs are assembled and in which orientations the motifs and elements are inserted. This is necessary whether the motifs or elements utilized are based on synthetic sequences or based on optimized sequences. While the optimization of promoters has resulted in improvements in expression, the promoter only represents one aspect of the regulatory elements needed in a fully functional and optimized expression vector.

The sequence of the 5' untranslated region (5'UTR) of messenger RNA (mRNA) plays an important role in post-transcriptional regulation of gene expression from eukaryotic mRNA. The variability of sequences and the importance of various motifs and characteristics of the 5'UTR region of mRNA have been documented (Kozak, *J. Mol. Biol.* (1994) 235:95-110), and Kozak, *Gene* (2005) 361:13-37). The nature of the 5'UTR plays a role in message stability and translation efficiency. The stability and translatability of a given mRNA will impact the ability to effectively express recombinant proteins. Therefore, the design of expression vectors for the optimal production of recombinant proteins requires that the 5'UTR be evaluated for its ability to function in an efficient manner in a given host cell system. The 5'UTR as described is an important part of the mRNA which is encoded by the DNA sequence contained in the 3' end of gene promoters. Hence, in the context of defining the DNA sequence of the promoter it is generally inclusive of 5'UTR sequence (the region from the INR to the initiator methionine codon).

The sequences of the 3' untranslated region (3'UTR) of mRNA, along with the 5'UTR, play important roles in post-transcriptional regulation of gene expression. The nature of the 3'UTR plays a role in message stability, transport from the nucleus to the cytoplasm, and sub-cellular localization. Each of these factors can have an impact on the efficiency of translation of a given message and ultimately on the level of protein expression. Therefore, the design of expression vectors for the optimal production of recombinant proteins requires that the 3'UTR be evaluated for its ability to function in an efficient manner in a given host cell system.

Most proteins that are secreted from cells contain an N-terminal signal sequence that directs the protein into the cell's secretion pathway. In eukaryotic cells, the secretion signal or signal peptide interacts with the endoplasmic membrane to initiate the secretion process. The eukaryotic signal sequence has been divided into three structural regions, basic, hydrophobic, and polar, starting from the N-terminus and proceeding to the C-terminus respectively (von Heijne, *Nuc. Acids Res.* (1986) 14:4683-4690) and (Bendtsen et al., *J. Mol. Biol.* (2004) 340:783-795). Over the years numerous secretion signals have been identified and used to direct the secretion of recombinant proteins. Although many different signal sequences have been used and shown to be functional, few studies have been reported that define optimal sequences for a given cell type. The general characteristics and rules related to the three structural regions are well established, as detailed by von Heijne (*Nuc. Acids Res.* (1986) 14:4683-4690) and by Bendtsen et al. (*J. Mol. Biol.* (2004) 340:783-795), however, little comparative experimental data exist as to what constitutes an optimal secretion signal. Most published reports deal with the characterization and optimization of gram positive bacterial or yeast secretion signals (Le Loir et al., *Microb. Cell Fact.* (2005) 4:2 and Hofmann and Schultz, *Gene* (1991) 101:105-111). One report that describes the optimization of the IL-2 secretion signal clearly demonstrates the benefits of optimization (Zhang et al., *J. Gene Med.* (2005) 7:354-365).

The development of optimized expression vectors for use in insect cells to generate stable cell lines capable of producing large quantities of high quality recombinant proteins requires the identification of appropriate regulatory elements, including but not limited to the core promoter element, that can be used to drive transcription and translation of the heterologous proteins to be expressed. Furthermore, synthetic regulatory elements can be designed and utilized to further optimize the functionality of the expression vectors. The disclosures of Lim et al., *Genes Dev.* (2004) 18:1606-1617, Kutach and Kadonaga, *Mol. Cell. Biol.* (2000) 20:4754-4764), and Juven-Gershon et al., *Biochem. Soc. Trans.* (2006) 34:1047-1050 are limited to the core promoter element, and specifically to novel or heterologous sequences and/or spacing of the TATA box, INR, MTE, and DPE motifs. Full optimization of regulatory control of expression of recombinant proteins requires that multiple regulatory elements, not just motifs in the core promoter, be optimized.

While many regulatory elements are known for *Drosophila* as well as other insects, what constitutes optimal elements for the expression of heterologous proteins in insect cells is not known. Current technology and methods provide the potential to assemble regulatory elements into an expression vector based on the current body of knowledge. While the potential exist, it is common knowledge that not all attempts to do so result in success. The recombinant expression regulatory elements that work in one cell type do not always work in another cell type. For example, Olsen et al. (*Cytotechnol.* (1992) 10:157-167) evaluated the ability of a series of promoters to drive the expression of a heterologous protein in S2 cells and found that only the *Drosophila* MtnA resulted in microgram yields of product despite the fact that all of the promoters tested had been shown to work in other cell types. In another example, a *Bombyx mori* expression vector based on the IE promoters which works well in Lepidopteron cells (Farrell et al., *Biotechnol. Bioeng.* (1998) 60:656-663) fails to adequately drive expression of heterologous proteins in S2 cells (unpublished data). Therefore, a systematic evaluation is required to determine the potential to consistently express high levels of high quality heterologous proteins using S2 cells. In the biotechnology field, the ability to efficiently produce recombinant proteins at a favorable cost of goods is key to success. In order to achieve this goal using *Drosophila* S2 cells, further development of suitable expression vectors is needed.

The combination of multiple regulatory elements in an appropriate manner such that an additive benefit is achieved can further enhance the utility of the expression vector. Therefore, the technical problems to be solved are: (1) identification of regulatory elements for inclusion in expression vectors that are capable of driving expression of large quantities of high quality recombinant proteins in insect cells, (2) the design of synthetic versions of functional regulatory elements that have improved function, and (3) determining the optimal combination of multiple regulatory elements such that the combination results in an additive increase in the productivity of the protein expression. Further improvements in stable insect expression systems could potentially provide new platforms for the manufacture of proteins where large quantities of high quality protein are needed, such as in cell based systems for production of subunit vaccines against infectious diseases, for example influenza, or organisms with bioterrorism potential.

SUMMARY OF THE INVENTION

The invention provides expression vectors composed of synthetic and optimized regulatory elements that are combined to provide for high levels of expression of heterologous recombinant proteins in stably transformed insect cells. Specifically the invention is directed at expression of heterologous proteins when *Drosophila melanogaster* S2 cells are used as the host cell.

The pHBI-10 (SEQ ID NO:10) and pHBI-11 (SEQ ID NO:11) expression vectors described below are composed of five regulatory elements: proximal promoter, core promoter, 5'UTR, secretion signal sequence, and 3'UTR. The five elements are operably linked to create an expression cassette. The regulatory control elements contained in the expression cassettes are each optimized for use in *Drosophila* S2 cells; however, the nucleotide sequences that define the regulatory elements of the present invention are not found naturally in the *Drosophila* genomic sequence due to the optimized or synthetic nature of these sequences.

The expression vectors of the present invention are capable of directing the high level expression and secretion of heterologous proteins into the culture medium of transformed cells. Specifically, the described expression vectors contain 1) synthetic, optimized inducible, proximal promoter, 2) synthetic optimized RNA polymerase II core promoter, 3) truncated and optimized 5'UTR sequence, 4) synthetic, optimized secretion signal sequence, and 5) optimized 3'UTR sequence.

The invention also provides methods for cloning heterologous gene sequences into the optimized expression vectors and utilizing the optimized expression vectors to transform insect cells which results in the secretion of high levels of recombinant proteins that maintain native-like structure.

BRIEF DESCRIPTION OF THE DRAWINGS

FIG. 1. Sequence of the 3XR MRE-3XR MRE-SCP1-TolloMTE-Δ111 synthetic promoter (SEQ ID NO:12). Each of the regulatory motifs in the proximal and core promoter regions are indicated.

FIG. 2. Sequence of the 3XR MRE-3XR MRE-SCP7 synthetic promoter (SEQ ID NO:13). Each of the regulatory motifs in the proximal and core promoter regions are indicated FIG. 3. Comparison of pMTtPA, pHBI-10, and pHBI-11 Expression Vectors. The regulatory control elements for each vector are listed in FIG. 3.

FIG. 4. pHBI-10 plasmid map. The plasmid map of the full plasmid is shown. The pHBI-10 vector contains the TolloMTE-Δ111 synthetic core promoter.

FIG. 5. pHBI-11 plasmid map. The plasmid map of the full plasmid is shown. The pHBI-11 vector contains the SCP7 synthetic core promoter.

DETAILED DESCRIPTION OF THE INVENTION

The invention provides a series of optimized regulatory elements that have been combined into expression vectors that are used to drive the expression of high levels of high quality proteins from insect cells that have been stably transformed with these expression vectors carrying the gene sequence of the protein to be expressed. The use of synthetic and optimized regulatory elements in a single expression vector results in the ability to reliably and quickly produce recombinant proteins in a stable insect expression system at levels that provide a favorable cost of goods for the expressed product.

The term "regulatory element" (or "regulatory control element" or "control element", or simply "element") refers to a segment of an expression vector, that has a known function in the transcriptional and/or translational processes involved in expression of the resultant protein product of a given gene sequence. Regulatory element is distinguished from the term "regulatory motif" (or simply, "motif") which refers to a defined sequence that acts either as a binding site or marks a transitional site. In general, regulatory elements are composed of multiple regulatory motifs.

The term "synthetic" regulatory element refers to sequences that are not found to occur naturally. More specifically, the synthetic elements described here in are not found in the genomic sequence of *Drosophila*. The term "optimized" regulatory element refers to sequences that were derived from naturally occurring sequences and have been altered to enhance their functions. The specific sequences of the optimized regulatory elements do not represent naturally occurring variants of the sequences from which the optimized sequences are derived; therefore, the optimized regulatory elements (and motifs therein) can also be referred to as synthetic.

"Expression cassette" means the combination of promoter elements with other transcriptional and translational regulatory control elements which are operably linked. A heterologous gene sequence can be inserted into the expression cassette for the purpose of expression of said gene sequence. The expression cassette is capable of directing transcription which results in the production of an mRNA for the desired gene product. The expression cassette is inserted into a plasmid to produce an expression vector. Such an expression vector directs expression of the heterologous protein in host cells.

The term "transformed" refers to the DNA-mediated transformation of cells. This refers to the introduction of plasmid DNA into insect cells in the process of generating stable cell lines following the integration of the introduced DNA into genome of the cells. This term is used in place of the term "transfection" which is often used in the same context. We use the term transformation for the introduction of plasmid DNA to cultured cells to distinguish from the introduction of viral DNA into cultured cells which was originally referred to as transfection. As there is no viral DNA sequences in the expression vectors of the present invention and the introduction of these expression vectors into the cells does not result in the production of virus-like particles or cell lysis the term transformed is preferred.

"Expression" or "expressed" means the production of proteins using expression vectors and host cells, for instance, Drosophila S2 cells to produce a recombinant protein product that is readily detectable as a cell associated product or as a secreted product in the culture medium.

"Secretion" means secretion of an expressed recombinant protein from cultured host cells into culture medium. The expressed and secreted protein is the result of a given gene sequence being operably linked to an expression cassette such that the sequence codes for the given protein.

The term "product" refers to any recombinant protein, full length or subunit thereof, which is expressed by a host cell into which an expression vector carrying the gene sequence encoding the product has been introduced.

Insect cells are an alternative eukaryotic expression system that provides the ability to express properly folded and post-translationally modified proteins while providing simple and relatively inexpensive growth conditions. The use of stably transformed insect cell expression systems provide benefits over those based on baculovirus infection of the host insect cells. On this basis, S2 cells were selected as the insect host cells of choice. As a result, the efforts to optimize the expression vectors for stably transformed insect cells were based on data derived from the analysis of specific Drosophila genes as well as the complete Drosophila genome.

In a preferred embodiment of the invention, the core promoter of the expression vector is defined as the sequence spanning the transcription initiation site (INR), more specifically the sequence 35 to 45 nucleotides upstream and downstream of the INR (total length of 70 to 90 nucleotides). The "A" (adenine) nucleotide of the INR motif is designated +1. The core promoters of the invention contain a combination of motifs that is not found in nature. These core promoters are composed of known regulatory motifs; however, the combination of motifs is unique and several of the motifs in the core promoter of the invention are based on consensus sequence and further tuned for optimal function when combined to form the core promoter regulatory element. The known regions of importance in the core promoters of the expression vectors described herein are the TATA box, transcriptional initiation site (INR), motif ten element (MTE) and downstream promoter element (DPE). Promoters of the present invention, with synthetic core promoters which contain at least three of these four core regulatory motifs, are presented in SEQ ID NO:1, NO:2 and NO:3. In the present invention, the synthetic core promoters (SEQ ID NO:2 and NO:3) are capable of driving high levels of expression when joined with an appropriate upstream regulatory element such as a proximal promoter.

In yet another preferred embodiment of the invention, the 5'UTR sequence is defined as the sequence from the "A" (adenine) nucleotide of the INR motif to the nucleotide in the sequence that immediately precedes the initiating methionine codon. The 5'UTRs of the invention have a comparatively short 5'UTR and contains a Drosophila consensus Kozak sequence at the 3' end. The sequences that define the 5'UTR of the mRNA that results from transcription directed by the two synthetic core promoters of the present invention are presented in SEQ ID NO:4 and NO:5.

In another preferred embodiment of the invention, the upstream regulatory elements contained in the proximal promoter that drive transcription of the core promoter and results in high levels of expression, is a synthetic sequence composed of multiple metal responsive elements (MRE). This synthetic proximal promoter is composed of 2 sets of 3XMREs separated by 11 nucleotides. All of the MREs are oriented in a reverse direction relative to the start of transcription as depicted in FIGS. 1 and 2. The sequence of this synthetic proximal promoter is presented in SEQ ID NO:6.

In yet another preferred embodiment of the invention, an optimized secretion signal peptide sequence is provided. By varying the total length, the N-terminal basic region, and the composition of the hydrophobic region, an optimized signal peptide sequence was designed and synthesized for use in directing the secretion of expressed proteins into the culture medium of the transformed cells. Restriction sites that allow for the cloning of protein encoding sequences in the same reading frame with the secretion signal, and that do not negatively impact the secretion signal cleavage site, were also designed, and incorporated into the secretion signal sequence. The amino acid sequence of the synthetic secretion signal and the nucleotide sequence that encodes the peptide are presented in SEQ ID NO:7 and NO:8.

In yet another preferred embodiment of the invention, the 3'UTR sequence of the mRNA transcripts that are produced by the expression vectors of the invention is an optimized version of a native Drosophila 3'UTR sequence derived from the gene coding for a highly expressed and secreted protein called chitinase-like protein (Kirkpatrick et al., Gene (1995) 153:147-154). The chitinase-like protein is one of the most abundantly expressed and secreted protein in S2 cells. For this reason, the gene coding for the chitinase-like protein (CLP) was selected as a base for the optimization of the 3'UTR. The 3'UTR from the CLP gene does not contain the typical polyadenylation signal motif, AATAAA. Modifications and truncations made to this 3'UTR resulted in higher levels of expression. The sequence of the 3'UTR of the present invention is presented in SEQ ID NO:9.

In a more preferred embodiment of the invention, the combination of the five regulatory elements described above, which includes both transcriptional and translational elements, into a functional expression cassette that directs high level expression in S2 cells is disclosed. The sequences of two assembled expression cassettes that vary only in the core promoter sequences utilized are presented in SEQ ID NO:10 and NO:11.

Thus, the present invention provides expression vectors composed of synthetic and optimized regulatory elements that are capable of driving high levels of heterologous protein expression. The synthetic expression vectors, when used to express heterologous proteins in S2 cells enable the economic production of large quantities of high quality proteins. All synthetic, or a combination of synthetic and wild-type, or of synthetic and consensus, or of synthetic, wild-type, and consensus, regulatory control elements can be used in an expression cassette. The Examples below show that using all synthetic elements produce (or "drive") the highest levels of heterologous protein expression. Where less than all regulatory control elements are synthetic, the remaining elements are assumed to be wild-type elements (non-optimized) known in the art to work with a given type of host cell.

Although the descriptions presented above and the examples that follow are primarily directed at the use of the optimized expression vectors with Drosophila S2 cells, the vectors and methods can be applied to other insect cell lines that result in stable cell lines following transformation of host cells with plasmid DNA.

The following examples are offered by way of illustration and not by way of limitation.

EXAMPLES

The following examples describe the development of the synthetic expression vectors for use in insect cells. The examples demonstrate the ability to effectively express heterologous proteins in *Drosophila* S2 cells at levels that are commercially suitable for product development.

The examples demonstrate the ability of the individual regulatory elements to enhance the ability to express proteins in S2 cells and the efforts made to determine what changes contributed to the enhanced function of these elements. The results presented below demonstrate that different elements and modification of these elements can result in high levels of expression or in very little or no detectable expression. Thus, the selection of functional and effective regulatory elements must be determined thorough experimentation. Hence, the invention described herein is unique in that the expression cassette described is mostly synthetic in composition and directs high levels of protein expression.

Example 1

Use of Non-*Drosophila* Promoters to Drive Expression of Heterologous Proteins in *Drosophila* S2 Cells In an effort to identify alternative expression vectors capable of driving high levels of high quality products in S2 cells, expression vectors containing promoters derived from other insects were evaluated. For this work standard methods of culturing and transformation of S2 cells were utilized (Van der Straten, *Methods in Mol. and Cell Biol.* (1989) 1:1-8; Culp et al., *Biotechnology* (1991) 9:173-177; Kirkpatrick and Shatzman, In *Gene Expression Systems: Using Nature for the Art of Expression*, Eds. Fernandez and Hoeffler, Academic Press, (1999) 289-330). *Drosophila* S2 cells (Schneider, *J. Embryol. Exp. Morph.* (1972) 27:353-365) obtained from ATCC were utilized. The S2 cells have been adapted to growth in Excell 420 medium (SAFC, St Louis, Mo.) and all procedures and culturing described herein were in Excell 420 medium. Cultures are typically seeded at a density of $1 \times 10^6$ cells/ml and are passed between days 5 and 7. All cultures were incubated at 26° to 27° C. Expression plasmids into which genes of interest were inserted were transformed into S2 cells by means of the calcium phosphate method. The S2 cells were co-transformed with the pCoHygro plasmid for selection with hygromycin B at a ratio of 20 µg of expression plasmid to 1 µg of pCoHygro. Following transformation, cells resistant to hygromycin, 0.3 mg/ml, were selected. Once stable cell lines were selected, they were evaluated for expression of the appropriate products. For the evaluation of expression, 5 ml cultures of selected cell lines were seeded at $2 \times 10^6$ cells/ml and cultured in the presence of 0.2 mM copper sulfate at 26° C. for 7 days. Cultures were evaluated for expression of recombinant proteins in both the cell associated fractions and the culture medium. Proteins were separated by SDS-PAGE and either stained with Coomassie blue or blotted to nitrocellulose. Antibodies specific for the protein being expressed were used to probe the Western blots. Expression levels of 1 µg/ml (1 mg/L) or greater are readily detected in S2 cultures by Coomassie staining of SDS-PAGE gels.

The first insect promoter tested was the *Bombyx mori* (silk moth) cytoplasmic actin A3 promoter. This promoter has been used in an expression vector designed for high level of expression of stably transformed *B. mori* cells. The expression vector, pIE1/153A, contains in addition to the actin A3 promoter, the *B. mori* nuclear polyhedrosis virus (BmPNV) immediate early (ie-1) transcription factor and the homologous repeat 3 (HR3) region of BmNPV (Farrell et al. (*Biotech. Bioeng.* (1998) 60:656-663). Upon transformation of lepidopteron cells this expression vector has been shown to drive high levels of expression of recombinant proteins.

Various genes encoding subunit proteins such as the influenza hemagglutinin (HA) ectodomain (H3 HA-Ecto) and the malaria merozoite surface protein 1 p42 C-terminal fragment (MSP1-p42) were cloned into the pIE/153A vector and then the resulting recombinant plasmids were used to transform S2 cells. The H3 HA-Ecto sequence was derived from the H3N2 influenza strain A/Fujian/411/02 full length HA gene sequence (HA0) which encodes a protein of 566 amino acid residues. Specifically, the sequence utilized was derived from the nucleotide sequence in accession number ISDN38157 (ISD, www.flu.lanl.gov). The HA0 protein sequence contains a 16 amino acid secretion signal sequence at the N-terminus and a C-terminal membrane anchor. For the expression of the soluble H3 HA-Ecto, an N- and C-truncated molecule was expressed that is contained in the sequence from $Gln_{17}$ to $Gly_{526}$ (residue 175 of HA2, analogous to the C-terminus of the X31 crystal structure, Wilson et al., *Nature* (1981) 289: 366-373) of the full length protein. The H3 HA-Ecto nucleotide and amino acid sequences and expression are disclosed in detail in WO 2007/022425. The malaria MSP1-p42 sequence was derived from the FUP strain of *Plasmodium falciparum* (Genbank accession number M37213). The MSP-1 p42 encoding sequence obtained by PCR amplification encodes amino acids $Ala_{1333}$ to $Ser_{1705}$ of MSP-1 protein. The MSP1-p42 nucleotide and amino acid sequences and expression are disclosed in detail in WO 2006/026625.

The expression level for both the influenza and malaria subunit proteins were less than 1 µg/ml in S2 cells when expression was driven by the pIE/153A vector. On this basis of these results, the pIE/153A vector does not direct high level expression of recombinant subunit proteins when used to transform S2 cells.

The second insect promoter tested was the *Anopheles gambiae* (mosquito) metallothionein 1 promoter. To test this promoter for its ability to drive high level expression in S2 cells, the *Drosophila melanogaster* metallothionein promoter region (MtnA) was removed from the *Drosophila* expression vector pMTtPA and replaced with the *Anopheles* promoter. The pMTtPA expression vector and methods for its use for expression of recombinant proteins in cultured *Drosophila* cells are described in U.S. Pat. Nos. 5,550,043; 5,681,713; 5,705,359; 6,046,025. The plasmid pCoHygro described in U.S. Pat. No. 5,681,713 was used for hygromycin selection following co-transformation of S2 cells. The pMTtPA expression vector contains the following elements: the *Drosophila* metallothionein promoter (MtnA), the human tissue plasminogen activator (tPA) pre-pro signal sequence, and the SV40 early polyadenylation signal (Culp et al., Biotechnol. (1991) 9:173-177). The pCoHygro plasmid provides a selectable marker for hygromycin (van der Straten et al., *Methods in Mol. And Cell Biol.* (1989) 1:1-8). The hygromycin gene is under the transcriptional control of the *Drosophila* COPIA transposable element long terminal repeat. The pMTtPA vector was modified by deleting a 15 base pair BamHI fragment which contained an extraneous XhoI site. This modified vector, referred to as pMTtΔXho, allows for directional cloning of inserts utilizing unique Bgl II and XhoI sites. The vector was further modified by adding a HindIII restriction site and adding a *Drosophila* "consensus Kozak sequence" (Cavener, *Nuc. Acids Res.* (1987) 15:1353-1361) immediately preceding the initiator methionine codon of the tPA pre-pro signal sequence. Specifically the 12 nucleotide sequence in pMT-tPA, TGTGAAGCAATC (SEQ ID NO:14), immediately preceding the ATG was changed to AAGCTTAACAAC (SEQ ID NO:15; the first six nucleotides represents the HindIII restriction site and the second six nucleotides represent the *Drosophila* consensus Kozak sequence). This further modified vector is referred to as pMT-KtΔXho. The HindIII restriction site allows for the cloning of promoter sequences immediately preceding the translation start codon of the tPA pre-pro signal sequence. The *Anopheles* metallothionein promoter fragment was derived from sequence in the *Anopheles* genome database (www.ensembl.org/Anopheles_gambiae/) Specifically, the 1833 nucleotide promoter fragment represents the sequence upstream of the translation start codon of *Anopheles gambiae* metallothionein 1 gene (UniProtKB/TrEMBL entry name Q52P92_ANOGA). This gene can be found on Chromosome 2R at location 11,911,992-11,912,384 and is the homologue of the *Drosophila* MtnA gene. This nucleotide sequence was chemically synthesized (DNA 2.0, Menlo Park, Calif.) with the addition of a KpnI restriction site at the 5' end and a HindIII restriction site at the 3' end. The pMT-KtΔXho vector was digested with KpnI and HindIII to remove the *Drosophila* promoter and replaced with the *Anopheles* promoter. The resulting plasmid is referred to a pAgMT-KtΔXho. The H3 HA-Ecto sequence was then cloned into the pAgMT-KtΔXho vector.

The pAgMT-KtΔXho expression plasmid encoding the H3 HA-Ecto subunit protein was used to transform S2 cells. Upon selection of stable cell lines the cells were screened for expression of the secreted form of the H3 HA-Ecto protein when cultured in the presence of copper sulfate. The expression of the H3 HA-Ecto subunit driven by the *Anopheles* metallothionein promoter resulted in a uniform product of the expected molecular weight. While the expression of the H3 HA-Ecto driven by the *Anopheles* promoter was greater than that driven by the *Bombyx* promoter, the expression level was still considered low, approximately 1 µg/ml. This level is much lower than the level of H3 HA-Ecto expression when the *Drosophila* MtnA promoter is utilized, approximately 30 µg/ml.

Example 2

Design of Synthetic Core Promoter for *Drosophila* S2 Cells

The core promoter is defined as the minimal nucleotide sequence that is capable of direct transcriptional initiation of a given gene. The core promoter in eukaryotes is responsible for directing initiation by the RNA polymerase II complex. The core promoter is generally defined as the sequence spanning the transcription initiation site (INR), more specifically the sequence 35 to 45 nucleotides upstream and downstream of the INR (total length of 70 to 90 nucleotides). The 5'UTR encoding sequence starts at the INR and continues up to the translation initiating ATG codon. The 5' UTR encoding sequence is variable in length ranging from relatively short, 50 nucleotides, to rather long, several hundred nucleotides. As described previously, the core promoter generally contains one or more of the following sequence motifs, TFIIB recognition element (BRE), TATA box, initiator (INR), motif ten element (MTE), downstream promoter element (DPE), and downstream core element (DCE). In surveys of core promoters from several organisms including *Drosophila* it is clear that no universal core element exists; however, the INR motif is the most common (FitzGerald et al., Genome Biol. (2006) 7:R:53). In an effort to make a robust core promoter that is capable of directing transcription that leads to high levels of recombinant protein expression, a synthetic core promoter for *Drosophila* was designed that incorporated all of these elements. Consensus sequences for the various *Drosophila* regulatory motifs that make up the core promoter were utilized. These consensus regulatory motifs are described by Ohler et al. (*Genome Biology* (2002) 3:1-12; Kutach and Kadonaga, *Mol. Cell. Biol.* (2000) 20:4754-4764; Smale and Kadonaga *Ann. Rev. Biochem.* (2003) 72:449-479; Lim et al., *Genes Dev.* (2004) 18:1606-1617; FitzGerald et al. *Genome Biol.* (2006) 7:R53; Gershenzon et al. *BMC Genomics* (2006) 7:161)

To construct a *Drosophila* synthetic promoter, a core promoter containing the following *Drosophila* consensus regulatory motifs, BRE comprising GGGCGCC, TATA comprising TATAAA, INR comprising TCAGTC, MTE comprising CGAACGGAAC, and DPE comprising GGTTCG, was designed. The synthetic core promoter was fused to a portion of the *Anopheles* metallothionein 1 5'UTR. The fusion of the *Anopheles* metallothionein 1 5'UTR to the core promoter results in the position of the INR relative to the translation initiating ATG being analogous to that of the *Drosophila* MtnA promoter. This synthetic promoter was chemically synthesized and is referred to as synthetic core promoter 1 (SCP1). The sequence of the SCP1 promoter is listed as SEQ ID NO:1.

The chemically synthesized SCP1 included an XbaI site at its 5' end and a HindIII site at its 3' end for cloning into existing expression vectors.

The pMT-KtΔXho expression vector describe in Example 1 was further modified by inserting an XbaI restriction site seven nucleotides upstream of the TATA box sequence of the MtnA promoter. This plasmid is referred to as pMT-X-KtΔXho. This allowed for the removal of the MtnA core promoter (includes the 5' UTR) by digestion with XbaI and HindIII restriction enzymes and insertion of alternative core promoter and 5'UTR sequences. In this manner the SCP1 was inserted into the pMT-X-KtΔXho expression vector.

Example 3

Design of Proximal Promoter Containing Transcriptional Activator Elements Capable of Driving Expression of Heterologous Proteins in *Drosophila* S2 Cells In an effort to upregulate the level of transcription in core promoters which in turn results in high levels of expression in S2 cells, synthetic proximal promoters were designed to contain various transcriptional activator elements. The choice to develop synthetic proximal promoters rather than utilize naturally occurring proximal promoters for use in S2 cells is based on the results in Example 1 with the two insect promoters and also on the work of Olsen et al. (*Cytotechnology* (1992) 10:157-167) in which it was demonstrated that promoters of mammalian and virus origin do not work well in S2 cells. Therefore, the synthetic proximal promoters were designed to contain regulatory motifs derived from *Drosophila* promoters. The proximal promoter designs involved the assembly of repeats of individual regulatory motif consensus sequences or combinations of the different consensus regulatory motifs. The synthetic proximal promoters were evaluated for their ability to direct high levels of transcription when linked to core promoters. The first type of transcriptional regulatory element evaluated was the *Drosophila* DNA replication-related element (DRE). The promoters of *Drosophila* genes encoding DNA replication-related proteins contain the consensus DRE sequence 5'-TATCGATA. A specific DRE-binding factor, DNA replication-related element factor or DREF, binds to the DRE and positively regulates genes under the control DRE and results in high levels of expression.

Computational studies of *Drosophila* promoters (Ohler et al., *Genome Biology* (2002) 3:1-12) have shown that the DRE element is found in many *Drosophila* promoters. It is in fact one of the most common transcriptional elements. In the work of Hirose et al. (*Journal of Biological Chemistry* (1993) 268: 2092-2099) multiple copies of DRE were assembled and linked to a *Drosophila* MtnA core promoter controlling a luciferase reporter gene. The DREs upregulated the luciferase expression with the expression level increasing with the number of DREs added. In the design of a synthetic DRE containing proximal promoter, the sequence CTGCCTGCTATC-GATAGATTCAGG (SEQ ID NO:16; DRE consensus is in bold italics) was used. The synthetic DRE proximal promoter designs were as follows: 1XDRE, 2XDRE, and 4XDRE. The DRE containing proximal promoters were cloned into the pMT-X-KtΔXho vector describe in Example 2 by removal of the MtnA proximal promoter (KpnI-XbaI) and insertion of alternative proximal promoters immediately upstream of the MtnA core promoter. The DRE repeats were all in the same forward orientation (5' to 3'). These vectors are referred to as pDRE-X-KtΔXho. To evaluate the expression of recombinant proteins with these DRE expression plasmids the H3 HA-Ecto gene sequence described in Example 1 was inserted into these vectors and used to assess the level expression.

The pDRE-X-KtΔXho expression plasmids encoding the H3 HA-Ecto subunit protein were used to transform S2 cells. After selection of stable cell lines, they were screened for expression of the secreted form of the H3 HA-Ecto protein. All of the DRE proximal promoter constructs failed to result in any measurable H3 HA-Ecto expression.

The second type of transcriptional regulatory element evaluated was the *Drosophila* GAGA element. The *Drosophila* GAGA transcription regulatory factor is named for its ability to bind alternating $(GA)^n$ or $(CT)^n$ sequences (GAGA elements). This transcription factor is thought to increase gene expression by remodeling the chromatin structure around affected genes (Granok et al., *Current Biology* (1995) 5:238-241). GAGA elements are found in the promoters of a variety of *Drosophila* genes. It is found in the distal, proximal, and even core promoters of these genes (Soeller et al., *Mol. Cell. Biology* (1993) 13:7961-7970). In the work of Soeller et al. (1993) it was demonstrated that multiple GAGA elements could drive transcription of a core promoter.

Two proximal promoters were designed in which a single GAGA element was combined with DRE elements. These two designs were as follows: GAGA-2XDRE and 2XDRE-GAGA-2XDRE. As with the DRE proximal promoters these proximal promoters were inserted upstream of the MtnA core promoter in the expression vector pMT-X-KtΔXho. To evaluate the expression of recombinant proteins with these DRE-GAGA expression plasmids the H3 HA-Ecto gene sequence described in Example 1 was used as a reporter.

The expression plasmids with the DRE-GAGA combination promoters encoding the H3 HA-Ecto subunit protein were used to transform S2 cells. Upon selection of stable cell lines the cells were screened for expression of the secreted form of the H3 HA-Ecto protein. Both of these constructs also failed to result in any measurable protein expression.

The third type of transcriptional regulatory element evaluated was the *Drosophila* metal-responsive element (MRE). A specific MRE-binding factor, metal-responsive transcription factor or MTF-1, binds to the MRE and positively regulates genes under the control MRE and results in high levels of expression. The promoters of *Drosophila* genes regulated by MTF-1 contain the consensus MRE sequence 5'-TGCACAC.

It has been demonstrated that four copies of MREs can drive transcription of a minimal promoter (Zhang et al., *Mol. Cell. Biol.* (2001) 21:4505-4514).

Deletion analysis of the MtnA proximal promoter in the pMTtPAΔXho expression vector indicated that the deletion of an MRE with the sequence 5'-TCTTTTGCACACGC-CGGC (SEQ ID NO:17; consensus sequence is in bold italics) had the greatest impact on the strength of the MtnA promoter. Therefore, synthetic proximal promoters were designed containing one or more copies of the MRE sequence TCTTTTGCACACGCCGGC (SEQ ID NO:17). The synthetic MRE proximal promoter designs were as follows: 2X, 3X, 4X, 5X, 6X, 8X MREs. The MREs in these proximal promoter designs were all arranged in a 5' to 3' (forward) head-to-tail manner. As with the DRE proximal promoters the MRE proximal promoters were inserted upstream of the MtnA core promoter in the expression vector pMT-X-Kt-ΔXho. To evaluate the expression of recombinant proteins with these synthetic MRE promoter expression vectors, the H3 HA-Ecto gene sequence described in Example 1 was inserted into the vectors.

The expression plasmids with the MRE proximal promoters encoding the H3 HA-Ecto subunit protein were used to transform S2 cells. Upon selection of stable cell lines the cells were screened for expression of the secreted form of the H3 HA-Ecto protein. As these constructs contain MREs the evaluation of expression required that the cultures be induced with 0.2 mM $CuSO_4$, and cultured at 26° C. for 7 days.

Analysis of these S2 transformants revealed that as the number of MRE units increased, so did the level of gene expression up to a maximum with 6XMRE. The expression level decreased with 8X. Therefore, further analysis of expression utilizing a synthetic MRE proximal promoter was based on the 6XMRE design.

Using the 6XMRE synthetic proximal promoter, a series of expression constructs were made which allowed for a comparison of the native MtnA proximal promoter and the synthetic 6XMRE proximal promoter. In this series of expression constructs, the two proximal promoters were linked to three different minimal or core promoters: 1) *Drosophila* MtnA, 2) *Anopheles* MtnA and 3) SCP1 described in Example 2. The resultant six constructs were then linked with the H3 HA-Ecto reporter gene. Both the 6XMRE and the DmMtnA proximal promoter were able to drive the expression level of the flu gene to equivalent levels when comparing each of the given individual core promoters. For example the 6XMRE proximal-MtnA core and DmMtnA proximal-MtnA core resulted in equivalent levels of expression of the H3 HA-Ecto protein. This data with the 6XMRE proximal promoter indicates that a functional synthetic proximal promoter can be designed despite the failures with the first two transcriptional activators tested in this example.

The comparison of the 6XMRE and DmMtnA proximal promoter also revealed that the expression levels of H3 HA-Ecto in constructs containing the MtnA core promoter were approximately four times higher than those constructs containing the SCP1. Therefore, efforts were made to evaluate alternative core promoters as described in Example 4 and also to further optimize the synthetic core promoter as described in Example 5.

Example 4

Evaluation of a "Super Core Promoter" to Drive Expression of Heterologous Proteins in *Drosophila* S2 Cells Juven-Gershon et al. (*Nature Methods* (2006) 3:917-922) describe the design and analysis of a core promoter referred to as a "super core promoter" which directs high levels of RNA transcription by RNA polymerase II in metazoan host cells. The use of the same "super core promoters" is also disclosed in PCT application PCT/US2006/020394 (Kadonaga and Gershon, priority date 25 May 2005). The "super core promoters" described in these publications will be referred to as "Kadonaga core promoters" or "KCP". The Kadonaga core promoters consist of a minimal promoter containing INR and MTE elements, and optionally containing TATA and/or DPE elements, that are derived from several different *Drosophila* and viral genes. There are similarities in design to the KCP core promoters and the core promoters described in this Description since both rely heavily on the Genes and Development paper first describing the *Drosophila* MTE regulatory motif (Lim et al., *Genes Dev.* (2004) 18:1606-1617). The Kadonaga core promoters are described as being useful for heterologous protein expression in metazoan host cells, which include *Drosophila* S2 cells. Therefore, we at Hawaii Biotech, Inc. created three constructs containing the Kadonaga core promoters to test the functionality of the Kadonaga core promoters in the context of expression of heterologous proteins in stably transformed S2 cells.

The Kadonaga core promoter was synthesized with appropriate flanking restriction sites. The KCP synthetic sequence was inserted into the HBI-10 expression vector described in Example 9 and defined by SEQ ID NO:10 from which the proximal and core promoter sequences were removed. The resultant KCP/HBI-10 hybrid expression vector contains KCP linked to the 1R5L (SEQ ID NO:7) secretion signal, the H3 HA-Ecto reporter gene, and the Op-CLP-3'UTR (SEQ ID NO:9). The KCP/HBI-10 vector does not contain a proximal promoter. Therefore, two additional constructs were created from this "base KCP/HBI-10 hybrid vector" that, in addition to KCP, contained, in a first additional construct, the 6XMRE proximal promoter ("6xMRE/KCP/HBI-10"), and in a second additional construct, the Cytomegalovirus (CMV) enhancer ("CMV/KCP/HBI-10"); each proximal promoter was inserted immediately upstream of the KCP sequence. The CMV enhancer is the same as used in by Juven-Gershon et al. (*Nature Methods* (2006) 3:917-922, for which Dr. Kadonaga is the corresponding author). The three constructs were transformed into *Drosophila* S2 cells in triplicate and the expression level of H3 HA-Ecto was determined.

The two constructs CMV/KCP/HBI-10 and KCP/HBI-10 alone (no proximal promoter or enhancer) showed a minimal level of H3-HA-Ecto expression, i.e., <1 µg/ml Thus, this data indicates that 1) KCP alone provides for low level expression of a secreted protein and 2) this level of expression is not enhanced or increased by the CMV enhancer in transformed *Drosophila* S2 cells. The 6xMRE/KCP/HBI-10 construct resulted in the expression and secretion of the H3-HA-Ecto protein at 2-3 ug/ml in the crude supernatant. Previous experiments using the analogous construct of 6xMRE-SCP1 resulted in expression of the same H3-HA protein at 10 ug/ml or roughly 2-3 times higher than the KCP linked to the same 6XMRE proximal promoter. Since the only difference between the two constructs is the core promoter, it can be concluded that SCP1 described in Examples 2 and 3 provides for expression levels of secreted heterologous protein that are approximately 2-3 times greater than the expression that results from use of the Kadonaga core promoter and the 6xMRE proximal promoter in transformed *Drosophila* S2 cells. Use of a MRE or MRE-based proximal promoter was not disclosed in the Lim et al. (*Genes Dev.* (2004) 18:1606-1617) or Juven-Gershon et al. (*Nature Methods* (2006) 3:917-922) references.

The Kadonaga core promoter was optimized for use in mammalian cells. The data presented on the use of KCP in HeLa S3 cells was limited to transient transfections and the use of sensitive florescence assays; therefore, based on the results obtained with the KCP core promoters upon stable transformation of *Drosophila* cells, the use of transient transfection and sensitive reporter assays is not indicative of the ability to express and secrete heterologous proteins at high levels in all cell types. The design of the KCP includes elements of viral promoters such as CMV and AdML, which have classically been used for expression of proteins in mammalian cells. Nonetheless, a 2- to 3-fold increase in stable expression in *Drosophila* cells of secreted heterologous protein using SCP1 versus KCP is noteworthy and unexpected.

Example 5

Optimization of the Synthetic Core Promoter for Expression of Heterologous Proteins in *Drosophila* S2 Cells The original SCP1 design described in Example 2 contains a core promoter with a BRE, TATA box, INR, MTE, and DPE. Each of these motifs was removed individually and the effect of their removal on expression was evaluated. In each case, the expression level seemed to be slightly lowered. Attempts were made to further optimize the SCP by swapping the BRE, TATA, INR, MTE, and DPE motifs individually with the alternative sequences either containing an alternative sequence representing a given regulatory motif or with sequence lacking a regulatory motif at the equivalent position in the core promoter. For example, the wild-type *Drosophila* MtnA core promoter lacks BRE, MTE, or DPE motifs, yet, based on data presented in Example 3, the *Drosophila* MtnA core promoter is the strongest wild-type core promoter tested thus far. Removal of the BRE sequence in SCP1 and replacing it with "neutral" sequences resulted in no change in the expression level of a reporter gene product indicating the presence of the BRE was neutral, i.e. it had no apparent affect on transcription. In the case of the TATA box, the spacing between the SCP1 TATA and the INR was reduced by 3 nucleotides to match the spacing between the *Drosophila* MtnA TATA box and its corresponding INR. The 3 nucleotides removed (ACA) were those just immediately 3' of the TATA box. This change resulted in a slight lowering of the reporter gene expression level indicating that the spacing in the SCP1 was preferred over that in MtnA. The INR of SCP1 (TCAGTC) was changed to GCATCA, a three out of six nucleotide change. This change increased expression of the reporter gene product approximately 50%.

The SCP1 contains a 5'UTR encoding sequence that is 190 nucleotides in length. This portion of SCP1 is derived from the *Anopheles* Mtn gene. It was not known whether this sequence was beneficial or detrimental to transcription/expression. To determine the contribution of this sequence, two deletion constructs within this sequence were generated. The first removed 60 nucleotides of the sequence from the 3' end. This change resulted in a slight increase in expression level. The second removed 127 nucleotides of the sequence from the 3' end. This change resulted in an increase in expression level of approximately 2 fold. This truncated version of SCP1 is referred to as SCP1Δ111 and was used to further evaluate modifications to the core promoter.

The effects of the Tollo MTE on transcription levels were described by Lim et al. (*Genes Dev.* (2004) 18:1606-1617). Therefore, the consensus MTE used in SCP1Δ111 was changed to that found in the *Drosophila* Tollo promoter. The replacement of the consensus MTE with the Tollo MTE sequence resulted in an increase in expression level of approximately 2 to 3 fold. The insertion of the TolloMTE into the SCP1 core clearly had a very positive impact on expression levels. The core promoter with TolloMTE inserted is referred to as "SCP1-TolloMTEΔ111" and the promoter sequence containing this core promoter is listed as SEQ ID NO:2.

Further optimization of the core promoter was tested. A set of three new core promoters were designed which incorporated the positive aspects described in the previous three paragraphs that resulted in increased expression. The specific combination of the three key motifs and the 5'UTR element are: 1) the TATA motif, comprising TATAAA, and the spacing defined by the original SCP1 relative to the INR, 2) the INR sequence motif GCATCA, 3) the MTE sequence motif derived from *Drosophila* Tollo, and 4) the truncated 5'UTR (A111) element. The three new core promoters were designated SCP5, SCP6, and SCP7. All three of these core promoters lack the BRE sequence motif (comprising GGGCGCC when present) from SCP1. The three new core promoters differed in the sequence occupied by the DPE motif SCP5 contained the DPE from the *Drosophila* Tollo gene (GGACGC), SCP6 contained the consensus DPE used in SCP1 (GGTTCG) and SCP7 lacked a DPE motif and instead contained a "neutral filler" sequence to provide the same spacing relative to the SCP5 and SPC6 sequences. When SCP1, SCP5, SCP6, and SCP7 were compared in equivalent *Drosophila* S2 expression constructs, which only differed in their SCP sequences, the design of SCP7 resulted in the highest level of expression. The SCP7 sequence is listed as SEQ ID NO:3.

As discussed previously the sequence of the 5' untranslated region (5'UTR) of messenger RNA (mRNA) plays an important role in post-transcriptional regulation of gene expression from eukaryotic mRNA. The 5'UTR is defined by the region from the INR to the initiator methionine codon; hence, in the context of defining the DNA sequence of the promoter, it is generally inclusive of 5'UTR sequence. This is the case for the sequences listed for the SCP1-TolloΔ111 and SCP7 promoters. The 5'UTR that results from the SCP1-TolloMTEΔ111 promoter is referred to as the Δ111 5'UTR and listed as SEQ ID NO:4; the 5'UTR that results from the SCP7 promoter is referred to as the Δ111-7 5'UTR and listed as SEQ ID NO:5.

Example 6

Optimization of the Synthetic MRE Transcription Activator for Expression of Heterologous Proteins in *Drosophila* S2 Cells In nature, different combinations of transcriptional activators are found in the proximal promoters. On this basis, combinations of the GAGA and MRE elements described in Example 3 were created to determine if this combination of motifs would result in higher levels of transcription and ultimately higher levels of expression. Two GAGA-MRE proximal promoter designs were tested. They are as follows: GAGA-2XMRE and 2XMRE-GAGA-2XMRE.

The two GAGA-MRE proximal promoters were cloned into the area immediately preceding the various core promoters described in Example 3 utilizing the XbaI restriction site in the vector pMT-X-KtΔXho described in Example 3. Following the transformation and selection of stable S2 cell line with plasmids containing the GAGA-DRE proximal promoters the expression of the H3 HA-Ecto product was evaluated. The addition of the GAGA element to the MREs utilized did not increase or decrease expression levels compared to similar MRE constructs without the GAGA element.

In many proximal promoters, multiple transcription factor binding sites of the same type can often be found in both the forward and reverse orientations. This is true for the endogenous MREs found in the proximal promoters of the Mtn gene family of *Drosophila*. Therefore, in an effort to determine if the orientation of the MREs could improve the function of the proximal promoter, a series of synthetic MRE proximal promoter were created using various combinations of forward and reverse MRE sequences. The reverse (R) MRE is simply the reverse complement of the forward (F) MRE sequence described in Example 3. The reverse MRE has the sequence GCCGGCGTGTGCAAAAGA (SEQ ID NO:18; consensus MRE sequence is in bold italics). This series of new proximal promoters consisted of 3X repeats of the forward and/or reverse MREs arranged in various combinations. The combinations were as follows: 3XF MRE, 3XR MRE, 3XF MRE-3XR MRE, 3XR MRE-3XF MRE, 3XF MRE-3XF MRE, and 3XR MRE-3XR MRE. The spacing between the 3XMRE repeat units was 11 nucleotides. The sequence of the spacer is ATCAAACTAGA (SEQ ID NO:19).

As in Example 3, the forward and reverse containing MRE proximal promoters were inserted upstream of the MtnA core promoter in the expression vector pMT-X-KtΔXho. Similar expression plasmids containing the SCP1 core were also constructed. To evaluate the expression of recombinant proteins with these synthetic MRE promoter expression vectors, the H3 HA-Ecto gene sequence described in Example 1 was inserted into the vectors.

The expression plasmids with the MRE proximal promoters encoding the H3 HA-Ecto subunit protein were used to transform S2 cells. Following the transformation and selection of stable S2 cell line with plasmids containing the forward and reverse MRE combinations the expression of the H3 HA-Ecto product was evaluated. As these constructs contain MREs the evaluation of expression required that the cultures be induced with 0.2 mM $CuSO_4$, and cultured at 26° C. for 7 days.

Analysis of these S2 transformants revealed that when the different forward and reverse combinations were used they resulted in various levels of expression all of which were greater than the 6XMRE of Example 3. Even the 3XF MRE-3XF MRE resulted in slightly higher expression than the 6XMRE (~2 fold greater). This could be a result of the 11 nucleotide spacer which is the only difference between the 6XMRE and the 3XF MRE-3XF MRE proximal promoter sequences. The expression directed by the 3XF MRE-3XR MRE was approximately equal to that of 3XF MRE-3XF MRE. The expression directed by the 3XR MRE-3XF MRE was approximately 3 fold greater than the 6XMRE and the expression directed by the 3XR MRE-3XR MRE was approximately 4 to 5 fold greater than the 6XMRE. Therefore, the 3XR MRE-3XR MRE was selected as the proximal promoter to use in further constructs in which selected regulatory elements are combined to create a complete expression cassette composed of only synthetic or optimized elements as described in Example 9. The sequence of the synthetic proximal promoter 3XR MRE-3XR MRE is listed in SEQ ID NO:6.

Example 7

Design and Optimization of Synthetic Secretion Signal for Expression of Heterologous Proteins in *Drosophila* S2 Cells The secretion signal peptide plays an important role in the expression of proteins that are targeted for secretion from the cell. Therefore, the use of optimal sequences in an expression vector that directs recombinant proteins for secretion into the culture medium during production is important to the utility of such an expression vector. The example of secretion signal optimization presented by Zhang et al. (*J. Gene Med.* (2005) 7:354-365) clearly demonstrates the benefits of secretion signal optimization; however, this specific example applies to plants and it is not clear that the changes to the secretion signal described applies to other eukaryotic cell types. Therefore, a series of three secretion signals were designed to establish what types of changes to the sequence would result in increased expression of protein products into the culture medium of stably transformed S2 cells. The designs of the synthetic secretion signals followed the matrix table first described by von Heijne (*Nuc. Acids Res.* (1986) 14:4683-4690), and further refined by Bendtsen et al. (*J. Mol. Biol.* (2004) 340:783-795). The first set of three secretion signals tested all contained the same sequence in the cleavage region, varied sequence length in the hydrophobic region, and a varied number of charged residues in the basic region. The amino acid sequence of the three signal peptides tested are as follows with names in parenthesis:

M R T I I A L L L L T V S G A Q G ("1R4L", SEQ ID NO: 20)

M R T I I A L L L L *L* T V S G A Q G ("1R5L", SEQ ID NO: 21)

M R *R* T I I A L L L L L T V S G A Q G ("2R5L", SEQ ID NO: 22)

The 1R5L sequence is one amino acid longer (an additional "L" shown in bold italic typeface) than that of the 1R4L sequence as the length of the hydrophobic core has been increased, and the 2R5L sequence is one residue longer (an additional "R" shown in bold italic typeface) than the 1R5L sequence as an additional charged residue has been added to the basic region while maintaining the same hydrophobic core. The lengths of the 1R4L, 1R5L and 2R5L sequences are 17, 18 and 19 amino acids respectively. The three secretion signals were operatively linked to the H3 HA-Ecto domain gene in the pMtaf expression vector. The expression and secretion of the H3 HA-Ecto product utilizing these three secretion signals was compared to a similar H3 HA-Ecto domain construct where the tPA secretion signal was utilized. Upon transformation of S2 cells, selection of stable cell lines, and screening for expression levels of the product in the culture medium as described in Example 1, it was determined that the 1R5L resulted in the highest level of expression, approximately 2 fold more than the tPA containing construct, 3 fold more than the 2R5L containing construct, and 2 fold more than the 1R4L (equivalent to tPA) containing construct. Furthermore, a fortuitous mutation in the 1R5L sequence, Q to H (−2 position), resulted in an unexpected further increase in expression, approximately 2 fold, over the original 1R5L sequence. The 1R5L sequence containing the H residue is referred to as 1R5L(H) (SEQ ID NO:8) and was use in the final expression vectors disclosed in Example 9.

In the design of these secretion signal sequences, the hexanucleotide sequence AACAAC was placed immediately preceding the initiator methionine codon. This represents the consensus Kozak sequence for *Drosophila* described by Cavener (*Nuc. Acids Res.* (1987) 15:1353-1361).

The designs of the secretion signal sequences also evaluated the use of a T or S amino acid residue immediate following the G at the cleavage site. When the appropriate codon is selected for these residues, the sequence at the G/T and G/S cleavage sites encode for the restriction endonuclease cleavage sites KpnI and BamHI respectively. Both of these cleavage site sequences worked well. They both provide for convenient insertion of the desired protein encoding sequence to be fused in the same reading frame with the secretion signal.

The sequence of the 1R5L(H) optimized secretion signal is M R T I I A L L L L L T V S G A H G (SEQ ID NO:8). The preferred amino acid following the cleavage site is S. The nucleotide sequence encoding the optimized secretion signal and the corresponding amino acid sequence are listed as SEQ ID NO:7 and NO:8, respectively.

Example 8

Evaluation of an Alternative 3'UTR Element for Expression of Heterologous Proteins in *Drosophila* S2 Cells The 3'UTR of the gene and the mRNA play important roles at the transcriptional and translational levels of gene expression respectively (reviewed by Kloc et al., *Cell* (2002) 108: 533-544). Therefore, the use of optimal 3'UTR sequences in an expression vector that helps to improve polyadenylation, improves mRNA translocation from the nucleus to the cytoplasm, improves mRNA stability, and does not interfere with localization of the mRNA to the rough endoplasmic reticulum is important to the utility of an expression vector that directs products for release into the culture medium. It is for these reasons that it has been recommended that in the design of expression plasmids the 3'UTR be considered for optimization (van der Velden et al., *Biotechniques* (2001) 31:572-582).

The *Drosophila* pMTtPA expression plasmid utilizes the viral SV40 early 3'UTR sequence for termination and polyadenylation. While it is functional, there appears to be room to improve upon the use of this SV40 sequence. For example, the optimization of the 3'UTR for heterologous expression in insect systems was reported by Van Oers et al. (*J. Gen. Virol.* (1999) 2253-2262). They replaced the SV40 early 3'UTR with a baculovirus 3'UTR and the level of expression was increased. While they did not dissect the new 3'UTR to determine which parts contributed to the increase in expression, this work demonstrated that changes in the 3'UTR can improve expression of heterologous proteins. Unfortunately each expression system is unique and it is necessary to determine what constitutes an optimal 3'UTR for expression of secreted products in S2 cells.

The primary feature of most eukaryotic 3'UTR elements is the polyadenylation signal sequence (polyA signal), which is AATAAA. The polyA signal is involved in defining the 3' terminal cleavage site of the newly transcribed mRNA in the nucleus and at which polyadenylation occurs. In some 3'UTR's conserved sequences are observed immediately downstream of the cleavage site. These sequences are referred to as downstream sequence elements (DSE) and are believed to assist in defining the 3'UTR cleavage site.

The SV40 early 3'UTR that is present in the pMTtPA vector, and derivates, is 138 bases long and contains two putative polyA signals. The cleavage site for the addition of the polyA tail occurs at nucleotide 96. In the sequence between nucleotide 96 and 138 there are sequences that are thought to represent DSE motifs which would aid in cleavage.

In an effort to identify a 3'UTR sequence that would result in higher levels of expression, the 3'UTRs on many *Drosophila* genes where evaluated. The primary criteria were that the 3'UTR be approximately 100 nucleotides in length and be derived from a gene that encodes for a secreted product. The *Drosophila* Chitinase-Like Protein (CLP) described by Kirkpatrick et al. (*Gene* (1995) 143:147-154) is one of the most abundant secreted proteins from S2 cells and meets these criteria. This 3'UTR does not have a polyA signal that conforms to the AATAAA sequence. Kirkpatrick et al. suggest that the polyA signal is either at an AATATA or CATAAA.

In Kirkpatrick et al. (1995) the CLP 3'UTR cleavage site is defined by the position at which the polyA sequence is added to the mRNA, nucleotide 106. Based on the CLP cDNA clone LD21619 from the *Drosophila* Gene Collection (Berkeley *Drosophila* Genome Project, www.fruitfly.org/DGC/) the cleavage site is 7 to 11 nucleotides further down stream. Sequence alignment of the Kirkpatrick et al. sequence, the LD21619 sequence and the corresponding sequence from the *Drosophila* genome sequence identified a signal nucleotide error in the Kirkpatrick et al. sequence at nucleotide 43, A to G change. This change results in a sequence of AAGAAAA ("variant polyA signal") rather than AAAAAAA. There is also another AAGAAA sequence in the CLP 3'UTR. Based on the position of these AAGAAA sequences, the inventors postulated that one of these may be able to serve as the polyA signal, the second one being the most likely. For initial testing of the CLP 3'UTR in an expression vector, a fragment that of 117 nucleotides in length was selected. This fragment contains both of the AAGAAA variant polyA signals. Also, based on the alignment of the different sources of CLP sequences, this 117 fragment would allow for cleavage at either of the suggested cleavage sites, i.e., near each of the two variant polyA signals.

The 117 nucleotide CLP 3'UTR sequence was added to the expression vector pMTtPAΔXho from which the SV40 early 3'UTR was removed. The insertion of the 117 nucleotide CLP 3'UTR resulted in a 1.5 fold increase in expression of the reporter H3 HA-Ecto protein. In an effort to establish if the AAGAAA sequences serve as the polyA signal, the G residues in the two putative signals were mutagenized to T residues to match the consensus polyA sequence. This change resulted in a three-fold increase in expression as compared the equivalent expression vector with to SV40 early 3'UTR. In further experiments, both of the putative polyadenylation sites in the CLP 3'UTR were mutated to disrupt the sequences (first AAGAAA change to ACGCAA and the second AAGAAA changed to AATGAA). These changes resulted in a dramatic decrease in expression level. This further supports that at least one of these putative polyadenylation signals serves as the polyA signal.

To determine if additional down stream sequence was necessary to function as a DSE, the 3'UTR was extended another 20 nucleotides based on genomic sequence at the corresponding location. The extended 3'UTR lowered the expression level 2 to 3 fold, which was unexpected.

Based on these results the 117 nucleotide CLP-3'UTR with the two G to T mutations was selected for use in building an expression vector combining multiple regulatory elements described in Example 9. This optimized 3'UTR results in higher levels of expression and is referred to as Op-CLP-3'UTR. The sequence of the Op-CLP-3'UTR is listed as SEQ ID NO:9.

Example 9

Evaluation of Expression Vectors Containing Combinations of Regulatory Elements for Enhanced Expression of Heterologous Proteins in *Drosophila* S2 Cells In order to create an optimized expression vector for expression of recombinant protein products in S2 cells each of the following five regulatory elements are required: proximal promoter, core promoter, 5'UTR, secretion signal, and 3'UTR. Ideally each of these five elements is optimized and the combination of the elements will result in an expression cassette that results in higher levels of product expression. In the previous Examples, the following optimized elements were identified: the synthetic proximal promoter 3XR MRE-3XRMRE, the synthetic core promoters SCP1-TolloMTEΔ111 and SCP7, the truncated 5'UTR with the consensus Kozak sequence, the synthetic secretion signal 1R5L (H), and the optimized 3'UTR Op-CLP-3'UTR.

As a first step to evaluate combinations of these optimized regulatory elements the 1R5L secretion signal and the Op-CLP-3'UTR where used to replace the tPA secretion signal and SV40 early 3'UTR, respectively, in the pMT-X-Kt-ΔXho described in Example 3. The expression vector containing these two optimized elements is referred to as pHBI-5. Reporter genes (e.g., H3 HA-Ecto) were cloned into pHBI-5 and their expression was evaluated. Generally, the expression levels were 1.5 times greater than the expression level seen for the same reporter genes cloned into pMT-X-KtΔXho indicating that the improvements seen individually by the 1R5L secretion signal and Op-CLP-3'UTR were not additive; however, the expression levels were still higher than that driven by the pMT-X-KtΔXho vector.

Two expression cassettes were assembled containing all five elements. The two cassettes differed in regard to which of the two core promoters were used. The first cassette contains the SCP1-TolloMTEΔ111 core promoter and the second cassette contains the SCP7 core promoter. These expression cassettes are referred to as HBI-10 and HBI-11, respectively. The sequences of the entire cassettes are listed in SEQ ID NO:10 (HBI-10) and SEQ ID NO:11 (HBI-11). FIGS. 1 and 2 illustrate the sequence of the proximal promoter and core promoter regions of HBI-10 and HBI-11 respectively and are fully annotated. The differences of the HBI-10 and HBI-11 relative to pMTtPA are summarized in tabular form in FIG. 3.

The HBI-10 and HBI-11 expression cassettes were inserted into the pBR322 cloning vector to create the S2 cell expression vectors pHBI-10 and pHBI-11. The plasmid maps for these two S2 cell expression vectors are shown in FIGS. 4 and 5 respectively.

Evaluation of the expression of the H3 HA-Ecto product utilizing the pHBI-10 and pHBI-11 expression vectors revealed that the pHBI-11 resulted in an approximately 3 fold greater level of expression relative to pMT-X-KtΔ vector and the pHBI-10 resulted in an approximately 2 fold greater level of expression relative to the expression of the same H3-HA-Ecto product directed by pMT-X-KtΔ vector.

REFERENCES

Apuya N, Kwok S, Alexandrov N, Tatrinova T, Fang Y, Pennell R, Lu Y P, Medrano L, Cook Z, Feldmann K. Promoter, Promoter Control Elements, and Combinations, and uses Thereof. U.S. Patent No.: US 2006/0090216 A1. Pub. Date; Apr. 27, 1006.

Bendtsen J D, Nielsen H, von Heijne G, Brimal S. Improved prediction of signal peptides: SignalP 3.0. J Mol Biol 2004; 340:783-795.

Bernard A R, Kost T A, Overton L, Cavegn C, Young J, Bertrand M, Yahia-cherif Z, Chabert C and Mills A. Recombinant protein expression in *Drosophila* cell line: comparison with the baculovirus system. Cytotechnology. 1994; 15:139-144.

Bin L, Tsing S, Kosaka A H, Nguyen B, Osen E G, Bach C, Chan H and Barnett J. Expression of human dopamine B-hydroxylase in *Drosophila* Schneider 2 cells. Biochem. J. 1996; 313:57-64.

Butler, J E F, Kadonaga J T. The RNA polymerase II core promoter: a key component in the regulation of gene expression. Genes Dev. 2002; 16:2583-2592.

Cavener D R. Comparison of the consensus sequence flanking translational start sites in *Drosophila* and vertebrates. Nucleic Acids Research. 1987; 15(4):1353-1361.

Culp J S, Johansen H, Hellmig B. Regulated expression allows high level production and secretion of HIV gp120 envelope glycoprotein in *Drosophila* Schneider cells. Biotechnology. 1991; 9:173-177.

Deo Y K, Park E Y. Multiple co-transfection and co-expression of human β-1,3-N-acetylglucosaminyltransferase with human calreticulin chaperone cDNA in a single step in insect cells. Biotechnol. Appl. Biochem. 2006; 43: 129-135.

Edelman G M, Meech R, Owens G C, and Jones F S. Synthetic promoter elements obtained by nucleotide sequence variation and selection for activity. Proc Natl Acad Sci. 2000; 97: 3038-3043.

Farrell P J, Lu M, Prevost J, Brown C, Behie L, Iatrou K. High-level expression of secreted glycoproteins in transformed lepidopteran insect cells using a novel expression vector. Biotechnology and Bioengineering. 1998; 60(6): 656-663.

FitzGerald P C, Sturgill D, Shyakhtenko A, Oliver B, Vinson C. Comparative genomics of *Drosophila* and human core promoters. Genome Biology. 2006; 7:R53.

Gardsvoll H, Werner F, Sondergaard L, Dano K, Ploug M. Characterization of low-glycosylated forms of soluble human urokinase receptor expressin in *Drosophila* Schneider 2 cells after deletion of glycosylation-sites. Protein Expression and Purification. 2004; 34:284-295.

Gershenzon N I, Trifonov E D, Ioshikhes I P. The features of *Drosophila* core promoters revealed by statistical analysis. BMC Genomics. 7:161.

Granok H, Leibovitch B A, Shaffer C D, Elgin S C R. Ga-ga over GAGA factor. Current Biol. 1995; 5: 238-241.

Hirose F, Yamaguchi M, Handa H, Inomata Y, Matsukage A. Novel 8-base pair sequence (*Drosophila* DNA replication-related element) and specific binding factor involved in the expression of *Drosophila* genes for DNA polymerase a and proliferating cell nuclear antigen. J Biol Chem. 1993; 268: 2092-2099.

Hofmann K J, Schultz L D. Mutations of the α-galactosidase signal peptide which greatly enhance secretion of heterologous proteins by yeast. Gene. 1991; 101:105-111.

Ikonomou L, Schneider Y-J, Agathos S N. Insect cell culture for industrial production of recombinant proteins. Appl. Microbiol. Biotechnol. 2003; 62:1-20.

Incardona, J. P. and T. L. Rosenberry. Construction and characterization of secreted and chimeric transmembrane forms of *Drosophila* acetylcholinesterase: a large truncation of the C-terminal signal peptide does not eliminate glycoinositol phospholipid anchoring. Mol. Biol. of the Cell 1996; 7:595-611.

Ivey-Hoyle, M. Recombinant gene expression in cultured *Drosophila melanogaster* cells. Curr. Opin. Biotechnol. 1991; 2:704-707.

Johansen H A, van der Straten R, Sweet R, Otto E, Maroni G, Rosenberg M. Regulated expression at high copy number allows production of a growth-inhibitory oncogene product in *Drosophila* Schneider cells. Genes and Development. 1989; 3:882-889.

Juven-Gershon T, Hsu J Y, Kadonaga J T. Perspectives on the RNA polymerase II core promoter. Biochem Soc. Trans. 2006; 34:1047-1050.

Juven-Gershon T, Cheng S, Kadonaga J T. Rational design of a super core promoter that enhances gene expression. Nature Methods. 2006; 3:917-922.

Kadonaga J T and T Gershon. Optimized core promoters and uses therefor. Application PCT/US2006/020394. App published 30 Nov. 2006. Priority date 25 May 2005 (U.S. provisional 60/684,482).

Lim C Y, Santoso B, Boulay T, Dong E, Ohler U, Kadonaga J T. The MTE, a new core promoter element for transcription by RNA polymerase II. Genes and Development. 2004; 18: 1606-1617.

Kirkpatrick R B, Matico R E, McNulty D E, Strickler J E, Rosenberg M. An abundantly secreted glycoprotein from *Drosophila melanogaster* is related to mammalian secretory proteins produced in rheumatoid tissues and by activated macrophages. Gene. 1995; 153: 147-154.

Kirkpatrick R B and Shatzman A. *Drosophila* S2 System for heterologous gene expression. In Gene Expression Systems: Using Nature for the Art of Expression. Joseph M Fernandez and James Hoeffler editors. Academic Press. 1999; Pp. 289-330.

Kloc M, Zearfoss N R, Etkin L D. Mechanisms of subcellular mRNA localization. Cell. 2002; 108:533-544.

Kozak M. Features in the 5' non-coding sequences of rabbit α and β-globin mRNAs that affect translational efficiency. J. Mol. Biol. 1994; 235:95-110.

Kozak M. Regulation of translation via mRNA structure in prokaryotes and eukaryotes. Gene. 2005; 361:13-37.

Kutach A K, Kadonaga J T. The downstream promoter element DPE appears to be as widely used as the TATA box in *Drosophila* core promoters. Mol. Cell. Biol. 2000; 20:4754-4764.

Le Loir Y, Azevedo V, Oliveira S C, Freitas D A, Miyoshi A, Bermudez-Humaran L G, Nouaille S, Ribeiro L A, Leclercq S, Gabriel J E, Guimaraes V D, Oliveira M N, Charlier C, Gautier M, Langella P. Protein secretion in *Lactococcus lactis*: and efficient way to increase the overall heterologous protein production. Microb. Cell Fact. 2005; 4:2.

Li X, Eastman E M, Schwartz R J, Draghia-Akli R. Synthetic muscle promoters: activities exceeding naturally occurring regulatory sequences. Nature Biotechnology. 1999; 17: 241-245.

Lim C Y, Santoso B, Boulay T, Dong E, Ohler U, Kadonaga J T. The MTE, a new core promoter element for transcription by RNA polymerase II. Genes and Dev. 2004; 18: 1606-1617.

Lu M, Johnson R R, Iatrou K. Trans-activation of a cell housekeeping gene promoter by the IE1 gene product of baculovirus. Virology. 1996; 218:103-113.

Lu M, Farrell P J, Johnson R, m Iatrou K. A baculovirus (BmNPV) repeat element functions as a powerful constitutive enhancer in transfected insect cells. J. Biol. Chem. 1997; 272:30724-30728.

Modis Y, Ogata S, Clements D, Harrison S C. A ligand-binding pocket in the dengue virus envelope glycoprotein. Proc. Natl. Acad. Sci. USA. 2003; 100:6986-6991.

Modis Y, Ogata S, Clements D, Harrison S C. Structure of the dengue virus envelope protein after membrane fusion. Nature. 2004; 427(6972): 313-319.

Ohler U, LiaoG, Niemann H, Rubin G M. Computational analysis of core promoters in the *Drosophila* genome. Genome Biol. 2002; 3(12): research0087.1-00087.12.

Olsen M K, Rockenbach S K, Fischer H D, Hoogerheide J G, Tomich C S C. Stable production of an analog of human tissue plasminogen activator from cultured *Drosophila* cells. Cytotechnology. 1992; 10: 157-167.

Rud I, Jensen P R, Naterstad, Axelsson L. A synthetic promoter library for constituitive gene expression in *Lactobacillus plantarum*. Microbiology. 2006; 152: 1011-1019.

Schmetzer O, Moldenhauer G, Riesenberg R, Pires J R, Schlag P, Pezzutto A. 2005. Quality of recombinant protein determines the amount of autoreactivity against the tumor-associated epithelial cell adhesion molecule antigen: low frequency of antibodies against the natural protein. The Journal of Immunology. 2005; 174: 942-952.

Schmidt F R. Recombinant expression systems in the pharmaceutical industry. Appl Microbiol Biotechnol. 2004; 65:363-372.

Schneider I J. Cell lines derived from late embryonic stages of *Drosophila melanogaster*. J. Embryol. Exp. Morph. 1972; 27:353-365.

Smale S T, Kadonaga J T. The RNA polymerase II core promoter. Annu. Rev. Biochem. 2003; 72: 449-479.

Soeller W C, Oh C E, Kornberg T B. Isolation of cDNAs encoding the *Drosophila* GAGA transcription factor. Mol and Cell Biol. 1993; 13: 7961-7970.

Tornoe J, Kusk P, Johansen T E, Jensen P R. Generation of a synthetic mammalian promoter library by modification of sequences spacing transcription factor binding sites. Gene. 2002; 297: 21-32.

van der Straten A H, Johansen H, Rosenberg M, Sweet R W. Introduction and constitutive expression of gene products in cultures of *Drosophila* cells using hygromycin B selection. Methods in Mol And Cell Biol. 1989; 1:1-8.

van der Velden A W, Voorma H O, Thomas A A M. Vector design for optimal protein expression. BioTechniques. 2001; 31: 572-582.

von Heijne G. A new method for predicting signal sequence cleavage sites. Nuc Acids Res. 1986; 14:4683-4690.

van Oers M M, Vlak J M, Voorma H O, Thomas, A A M. Role of the 3' untranslated region of baculovirus p10 mRNA in high-level expression of foreign genes. J Gen Virol. 1999; 80:2253-2262.

Wilson I A, Skehel J J, Wiley D C. Structure of the haemagglutinin membrane glycoprotein of influenza virus at 3A resolution. Nature 1981; 289:366-673.

Xu T, Logsdon N J, Water M R. Structure of insect-cell-derived IL-22. Acta Crystallogr D Biol Crystallogr. 2005; 61(pt 7): 942-50.

Zhang L, Leng Q, Mixson A J. Alteration in the IL2 signal peptide affects secretion of proteins in vitro and in vivo. J. Gene Med. 2005; 7:354-365

---

We claim:

1. An expression vector for expression and secretion of heterologous proteins in cultured insect cells, comprising an expression cassette, wherein the expression cassette contains a synthetic promoter that is composed of proximal and core promoter elements that are operably linked within the expression cassette such that the insertion of a heterologous gene sequence will result in protein expression from cells stably transformed with the expression vector wherein the proximal promoter comprises the 3XR MRE-3XR MRE sequence shown in SEQ ID NO:6 and the core promoter comprises the SCP1-TolloMTEΔ111 sequence shown in SEQ ID NO: 2 or the SCP7 sequence shown in SEQ ID NO: 3.

2. The expression vector of claim 1, further comprising a synthetic 5'UTR element operably linked to the synthetic proximal promoter and core promoter such that the combination is capable of driving the expression of heterologous proteins.

3. The expression vector of claim 2, further comprising a synthetic secretion signal sequence operably linked to the synthetic proximal promoter, core promoter and 5'UTR elements such that the combination is capable of driving the expression and secretion of heterologous proteins.

4. The expression vector of claim 3, further comprising a synthetic 3'UTR sequence operably linked to the synthetic proximal promoter, core promoter, 5'UTR, and synthetic secretion signal sequence elements such that the combination is capable of driving the expression and secretion of heterologous proteins.

5. The expression vector of claim 2, wherein the 5'UTR element comprises the sequence shown in SEQ ID NO:4.

6. The expression vector of claim 2, wherein the 5'UTR element comprises the sequence shown in SEQ ID NO:5.

7. The expression vector of claim 3, wherein the synthetic secretion signal sequence comprises the 1R5L(H) encoding sequence shown in SEQ ID NO:7.

8. The expression vector of claim 4, wherein the synthetic 3'UTR comprises the Op CLP 3'UTR sequence shown in SEQ ID NO:9.

9. An expression vector for expression and secretion of heterologous proteins in cultured insect cells, comprising the expression cassette shown in SEQ ID NO:10.

10. An expression vector for expression and secretion of heterologous proteins in cultured insect cells, comprising the expression cassette shown in SEQ ID NO:11.

* * * * *

UNITED STATES PATENT AND TRADEMARK OFFICE
CERTIFICATE OF CORRECTION

PATENT NO. : 8,198,079 B2
APPLICATION NO. : 12/451145
DATED : June 12, 2012
INVENTOR(S) : David Edward Clements, Gordon V. L. Wang and Carolyn Weeks-Levy Page 1 of 1

It is certified that error appears in the above-identified patent and that said Letters Patent is hereby corrected as shown below:

In column 1, lines 6-12, under "RELATED APPLICATIONS" delete:

"This application is a § 371 National Stage Application of PCT/US2008/05514, filed 4 April 2008, which claims the benefit of U.S. provisional patent application serial number 60/926,621, entitled "Synthetic Expression Vectors for Insect Cells", filed on 26 April 2007, the disclosures and drawings of which prior application are hereby incorporated by referenced in their entirety."

and add:

This application is a § 371 National Stage Application of PCT/US2008/05514, filed 28 April 2008, which claims the benefit of U.S. provisional patent application serial number 60/926,621, entitled "Synthetic Expression Vectors for Insect Cells", filed on 26 April 2007, the disclosures and drawings of which prior application are hereby incorporated by reference in their entirety.

Signed and Sealed this
Thirty-first Day of July, 2012

David J. Kappos
*Director of the United States Patent and Trademark Office*